(12) United States Patent
Galdonik et al.

(10) Patent No.: US 8,092,483 B2
(45) Date of Patent: Jan. 10, 2012

(54) STEERABLE DEVICE HAVING A COREWIRE WITHIN A TUBE AND COMBINATION WITH A FUNCTIONAL MEDICAL COMPONENT

(75) Inventors: Jason A. Galdonik, Hanover, MN (US); Matthew F. Ogle, Oronoco, MN (US); James Pokorney, Northfield, MN (US); Kavitha Ganesan, Brooklyn Park, MN (US); Grace Wlodarski, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1177 days.

(21) Appl. No.: 11/072,001

(22) Filed: Mar. 4, 2005

(65) Prior Publication Data

US 2006/0200047 A1 Sep. 7, 2006

(51) Int. Cl.
*A61M 29/00* (2006.01)
(52) U.S. Cl. ........................................................ 606/200
(58) Field of Classification Search ................... 138/39; 604/73
See application file for complete search history.

(56) References Cited

U.S. PATENT DOCUMENTS

| | | | |
|---|---|---|---|
| 4,610,662 A | 9/1986 | Weikl et al. |
| 4,723,549 A | 2/1988 | Wholey et al. |
| 4,728,319 A | 3/1988 | Masch |
| 4,784,636 A | 11/1988 | Rydell |
| 4,790,812 A | 12/1988 | Hawkins, Jr. et al. |
| 4,794,928 A | 1/1989 | Kletschka |
| 4,873,978 A | 10/1989 | Ginsburg |
| 4,883,460 A | 11/1989 | Zanetti |
| 4,887,613 A | 12/1989 | Farr et al. |
| 4,994,067 A | 2/1991 | Summers |
| 5,011,488 A | 4/1991 | Ginsburg |
| 5,011,490 A | 4/1991 | Fischell et al. |
| 5,053,008 A | 10/1991 | Bajaj |
| 5,059,178 A | 10/1991 | Ya |
| 5,102,415 A | 4/1992 | Guenther et al. |
| 5,108,419 A | 4/1992 | Reger et al. |
| 5,152,277 A | 10/1992 | Honda et al. |
| 5,163,906 A | 11/1992 | Ahmadi |
| 5,211,651 A | 5/1993 | Reger et al. |
| 5,549,626 A | 8/1996 | Miller et al. |
| 5,599,307 A | 2/1997 | Bacher et al. |
| 5,720,764 A | 2/1998 | Naderlinger |

(Continued)

FOREIGN PATENT DOCUMENTS

WO WO 95/05209 2/1995

(Continued)

OTHER PUBLICATIONS

Feldman, "Transcatheter Aspiration of a Thrombus in an Aortocoronary Saphenous Vein Graft," Am. J. Cardiol. Aug. 1, 1987, 60(4), 379-380.

(Continued)

*Primary Examiner* — Nicholas Lucchesi
*Assistant Examiner* — Pritesh Patel

(57) ABSTRACT

An integrated guiding device has a tube and a corewire within the tube and a torque coupler. The torque coupler can couple the rotational motion of the tube with the rotational motion of the corewire. The wire can be moved longitudinally at least some amount relative to the tube. The device can further comprise a functional medical structure, such as an embolism protection structure. The device can be used in medical procedures, such as less invasive procedures within the cardiovascular system. Improved fiber based embolism protection devices comprise fiber bundles that are twisted prior to delivery.

24 Claims, 12 Drawing Sheets

U.S. PATENT DOCUMENTS

| | | | |
|---|---|---|---|
| 5,766,191 | A | 6/1998 | Trerotola |
| 5,810,874 | A | 9/1998 | Lefebvre |
| 5,814,064 | A | 9/1998 | Daniel et al. |
| 5,827,229 | A | 10/1998 | Auth et al. |
| 5,836,868 | A | 11/1998 | Ressemann et al. |
| 5,843,051 | A | 12/1998 | Adams et al. |
| 5,882,329 | A * | 3/1999 | Patterson et al. ............. 604/500 |
| 5,897,567 | A | 4/1999 | Ressemann et al. |
| 5,910,154 | A * | 6/1999 | Tsugita et al. ................ 606/200 |
| 5,911,725 | A | 6/1999 | Boury |
| 5,911,734 | A | 6/1999 | Tsugita et al. |
| 5,935,139 | A | 8/1999 | Bates |
| 5,938,645 | A | 8/1999 | Gordon |
| 5,941,869 | A | 8/1999 | Patterson et al. |
| 5,997,557 | A | 12/1999 | Barbut et al. |
| 6,010,522 | A | 1/2000 | Barbut et al. |
| 6,022,336 | A | 2/2000 | Zadno-Azizi |
| 6,066,149 | A | 5/2000 | Samson et al. |
| 6,135,991 | A | 10/2000 | Muni et al. |
| 6,142,987 | A | 11/2000 | Tsugita |
| 6,159,195 | A | 12/2000 | Ha et al. |
| 6,168,579 | B1 | 1/2001 | Tsugita |
| 6,203,561 | B1 | 3/2001 | Ramee et al. |
| 6,206,868 | B1 | 3/2001 | Pariodi |
| 6,238,412 | B1 | 5/2001 | Dubrul et al. |
| 6,258,115 | B1 | 7/2001 | Dubrul |
| 6,270,477 | B1 | 8/2001 | Bagaoison et al. |
| 6,361,545 | B1 | 3/2002 | Macoviak et al. |
| 6,454,741 | B1 | 9/2002 | Muni et al. |
| 6,485,500 | B1 | 11/2002 | Kokish |
| 6,485,502 | B2 | 11/2002 | Don Michael et al. |
| 6,514,273 | B1 | 2/2003 | Voss et al. |
| 6,527,746 | B1 | 3/2003 | Oslund et al. |
| 6,562,058 | B2 | 5/2003 | Seguin et al. |
| 6,569,148 | B2 | 5/2003 | Bagaoisan et al. |
| 6,596,011 | B2 | 7/2003 | Johnson et al. |
| 6,602,271 | B2 | 8/2003 | Adams et al. |
| 6,610,077 | B1 | 8/2003 | Hancock et al. |
| 6,620,148 | B1 | 9/2003 | Tsugita |
| 6,689,144 | B2 | 2/2004 | Gerberding |
| 6,805,692 | B2 | 10/2004 | Muni et al. |
| 6,911,036 | B2 | 6/2005 | Douk et al. |
| 7,052,500 | B2 | 5/2006 | Bashiri et al. |
| 7,229,464 | B2 | 6/2007 | Hanson et al. |
| 7,717,934 | B2 | 5/2010 | Kusleika |
| 2002/0035347 | A1 | 3/2002 | Bagaoisan |
| 2002/0055747 | A1* | 5/2002 | Cano et al. .................... 606/108 |
| 2002/0095141 | A1 | 7/2002 | Belef et al. |
| 2002/0169472 | A1 | 11/2002 | Douk et al. |
| 2003/0023263 | A1 | 1/2003 | Krolik et al. |
| 2003/0135232 | A1 | 7/2003 | Douk et al. |
| 2004/0006365 | A1 | 1/2004 | Brady et al. |
| 2004/0220611 | A1 | 11/2004 | Ogle |
| 2004/0254602 | A1 | 12/2004 | Lehe et al. |
| 2005/0021075 | A1 | 1/2005 | Bonnette et al. |
| 2005/0021152 | A1 | 1/2005 | Ogle et al. |
| 2005/0085847 | A1 | 4/2005 | Galdonik et al. |

FOREIGN PATENT DOCUMENTS

| | | |
|---|---|---|
| WO | WO 98/38930 | 9/1998 |
| WO | WO 02/055146 | 7/2002 |
| WO | WO 02/85092 | 10/2002 |

OTHER PUBLICATIONS

Galdonik, U.S. Appl. No. 10/979,439, filed Nov. 2, 2004, entitled "Steerable Device Having a Corewire Within a Tube and Combination with a Functional Medical Component."

Nakagawa et al., "A Retrievable Nitinol Vena Cava Filter: Experimental and Initial Clinical Results," J. of Vascular and Interventional radiology, May-Jun. 1994; 5:507-512.

Final Office Action dated Jul. 20, 2011 in U.S. Appl. No. 10/854,920.

Final Office Action dated May 9, 2011 in U.S. Appl. No. 11/406,853.

* cited by examiner

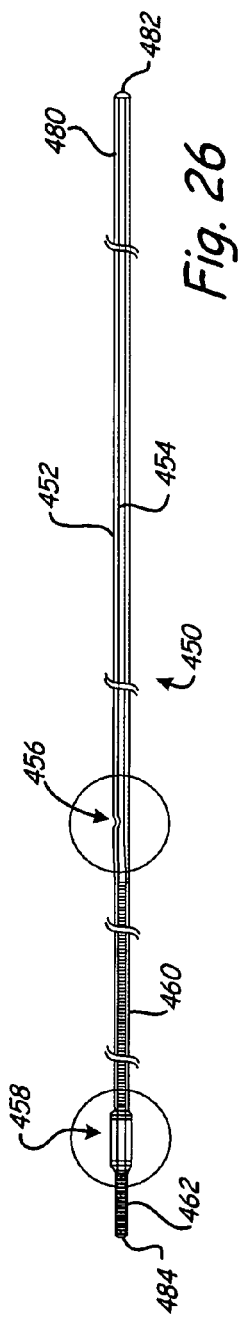
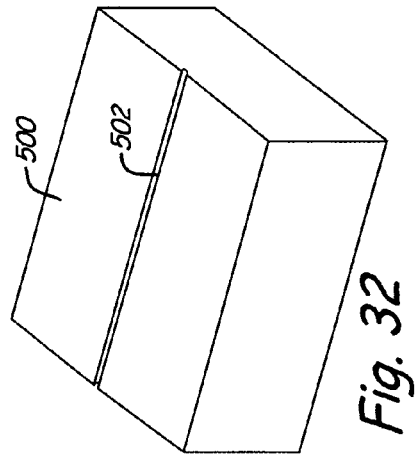
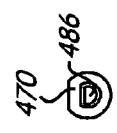
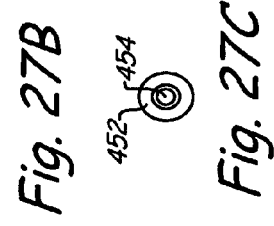
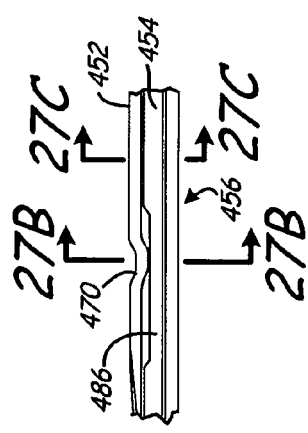
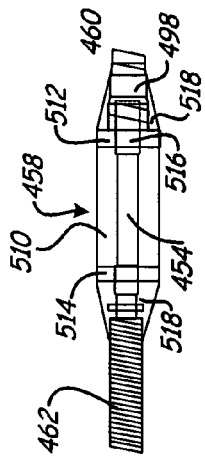
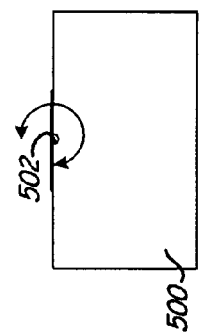
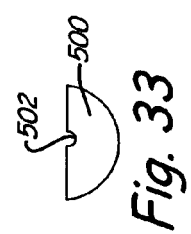

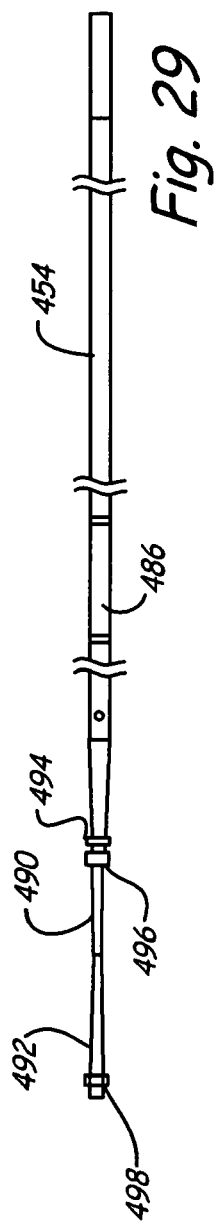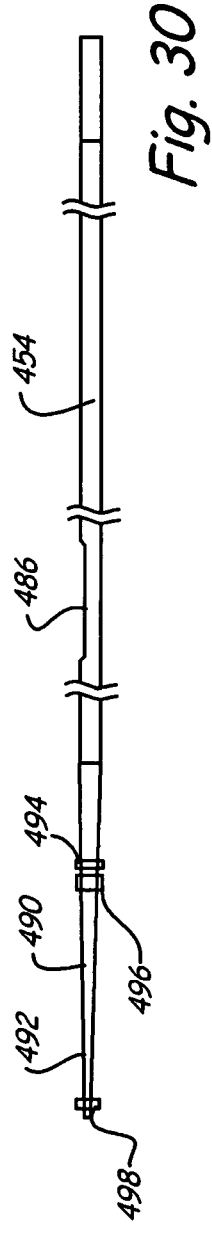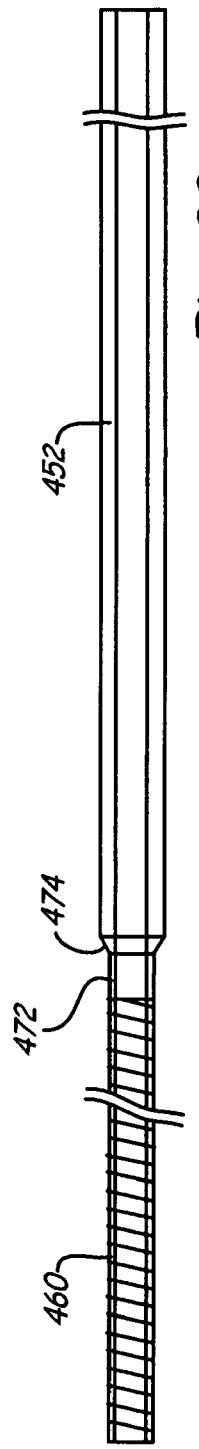

STEERABLE DEVICE HAVING A COREWIRE WITHIN A TUBE AND COMBINATION WITH A FUNCTIONAL MEDICAL COMPONENT

FIELD OF THE INVENTION

The invention relates to guiding devices for less invasive medical procedures and guide devices combined with additional functional medical components, such as actuatable medical structures, such as embolism protection structures. The invention further relates to procedures for using steerable guide devices alone and with functional medical components such as embolism protection structure. In addition, the invention relates to improved designs for embolism protection devices based on fibers.

BACKGROUND OF THE INVENTION

A variety of procedures are performed with less invasive approaches to reach distant locations within a patient's body. These procedures can be used, for example, for entry into the abdominal cavity or into the urinary track, or for reaching the patient's genitals. However, many of the procedures are performed within the cardiovascular system. For any of these procedures, a guidewire can be used to snake through the patient to position the tip of the guidewire at a desired location. A catheter and/or other medical devices can be positioned by sliding them over the guidewire to the appropriate location.

Generally, to position the guidewire, the guidewire traverses along a pathway, such as through vessels of the cardiovascular system, that has bends and branches. To navigate along the curves and branches, the guidewire and catheters are flexible. However, to steer the device to the desired location, some control generally should be possible with respect to directing the tip of the device for steering along curves and branches in the desired pathway. In particular, to guide the tip of the device, it is desirable to be able to apply torque to the end of the guidewire from the proximal end of the device under the control of the physician or other health care professional. Through the application of torque, the tip can be guided along a selected path within the patient.

Many less invasive procedures create the possibility of emboli formation as a result of the procedure. Also, some procedures may be specifically initiated to capture and/or remove emboli, which are generated or have a risk of being generated through another mechanism. An embolus can be any particle comprising a foreign and/or native material, which enters the vascular system or other vessel of the body with potential to cause occlusion of flow, e.g., blood flow. Emboli can be formed from aggregates of fibrin, blood cells or fragments thereof, collagen, cholesterol, plaque, fat, calcified plaque, bubbles, arterial tissue, and/or other miscellaneous fragments or combinations thereof. Emboli can lodge, for example, in the narrowing regions of medium size blood vessels that feed the major organs. Loss of blood flow to surrounding tissue causes localized cell death or microinfarcts. Cerebral microinfarcts can cause stroke leading to confusion, disturbance of speech, paralysis, visual disturbances, balance disturbances and even death. In the heart, emboli can cause myocardial infarcts, i.e. heart attacks. Myocardial infarction refers to the death of a section of myocardium or middle layer of the heart muscle. Myocardial infarction can result from at least partial blockage of the coronary artery or its branches. Blockage of capillaries associated with the coronary arteries can result in corresponding microinfarctions/microinfarcs. Resulting impairments are frequently short term but can be permanent.

Many clinical procedures can result in emboli including, for example, coronary, carotid, and peripheral interventions. In these cases, particulate matter, including, for example, plaque, debris and thrombus, can form emboli distal to the site of intervention. As a result, blood flow to the distal vascular bed can be diminished and periprocedural end-organ ischemia and infarction can result. Distal embolization of large particles produced at the time of such interventions as balloon inflation or stent deployment may obstruct large, epicardial vessels, and smaller particles (as small as 15-100 microns) can cause microinfarcts and/or myocardial infarctions and left ventricular dysfunction.

A significant reason for ischemic injury during percutaneous procedures can be generation of emboli that block smaller distal vessels. One approach to curb this complication has been to use pharmacological therapies during the time of the intervention. Limited therapeutic success has been reported with the use of calcium channel blockers, adenosine, and sodium nitroprusside (Webb, J G, Carere, R G, Virmani, R, Baim, D, Teirstein, P S, Whitlow, P, McQueen, C, Kolodgie, F D, Buller, E, Dodek, A, Mancini, G B, & Oesterle, S: Retrieval and analysis of particulate debris after saphenous vein graft intervention. *J Am Coll Cardiol* 2000, 34:468-475, incorporation herein by reference.). Glyoprotein IIb/IIIa inhibitors have been used for percutaneous coronary interventions to reduce platelet aggregation, but also fail to show meaningful long term clinical benefit. (Mathew, V, Grill, D E, Scott, C G, Grantham, J A, Ting, H H, Garratt, K N, & Holmes, D R, Jr. The influence of abciximab use on clinical outcome after aortocoronary vein graft interventions. *J Am Coll Cardiol* 1999, 34:1163-1169 and Mak, K H, Challapalli, R, Eisenberg, M J, Anderson, K M, Califf, R M, & Topol, E J: Effect of platelet glycoprotein IIb/IIIa receptor inhibition on distal embolization during percutaneous revascularization of aortocoronary saphenous vein grafts. EPIC Investigators. Evaluation of IIb/IIIa platelet receptor antagonist 7E3 in Preventing Ischemic Complications. *Am J Cardiol* 1997, 80:985-988, both of which are incorporated herein by reference.) Since embolization often develops from physical disruption of fibrotic plaque, a mechanism of therapeutic embolic protection specifically targeted at prevention of platelet aggregation and blood clotting may have little effect on these already-formed, embolizable plaques.

SUMMARY OF THE INVENTION

In a first aspect, the invention pertains to a catheter comprising a biocompatible material formed into a tube having at least one slot through the tube. The slot has a transverse component of the slot orientation. Also, the slot is positioned along the distal half of the catheter. Furthermore, the invention pertains to a method of forming a catheter. The method comprises cutting slots along a tubular member wherein the slots have a transverse component to the slot orientation.

In further aspects, the invention pertains to a medical system comprising a corewire, a tube over at least a portion of the corewire, a medical device and a pull element. The medical device is operably connected to the corewire and tube at or near their distal end. The pull element is operably connected to the corewire and tube at or near their respective proximal ends, and the pull element comprises a slide wherein the position of the slide controls the relative position of the corewire within the tube over a range of motion. The relative position of the corewire and the tube actuates the medical device, and the relative position of the corewire within the tube has at least one stable position effectively locking the relative position between the end points of the range of motion.

Moreover, the invention pertains to surgical system comprising a guide structure, a filter element and an aspiration catheter. The filter element is attached to the distal end of the guide structure. Also, the aspiration catheter is mounted over the guide structure. Generally, the aspiration catheter has a central lumen and comprises a suction element attached near the distal end of the aspiration catheter. The aspiration catheter has a length no more than about ¾ of the length of the guide structure.

In additional embodiments, the invention pertains to a method for delivering a filter into an exposed vessel of a patient. The method comprises inserting a filter element into a patient's vessel and applying aspiration during at least a portion of the process of removal of the filter element. The filter element is attached to a guide structure.

BRIEF DESCRIPTION OF THE DRAWINGS

FIG. 26 is a sectional side view of a specific embodiment of an integrated guiding device.

FIG. 27A is a fragmentary, expanded sectional side view of the torque coupler of the device of FIG. 26.

FIG. 27B is a sectional view of the torque coupler of FIG. 27A taken along line B-B.

FIG. 27C is a sectional view of the device of FIG. 27A taken along line C-C.

FIG. 28 is a sectional side view of the tube of the integrated guiding device of FIG. 26.

FIG. 29 is a top view of the corewire of the device of FIG. 26 separate from the tube.

FIG. 30 is a side view of the corewire of the device of FIG. 26 separate from the tube with the side view being 90 degrees rotated from the top view in FIG. 29.

FIG. 32 is a perspective view of a fixture block.

FIG. 33 is an end view of the fixture block of FIG. 32.

FIG. 34 is a fragmentary expanded end view of the channel within the fixture block of FIG. 32.

FIG. 35 is a fragmentary side view on an embolism protection structure of the integrated guiding device of FIG. 26.

DETAILED DESCRIPTION OF THE INVENTION

Figure 1:
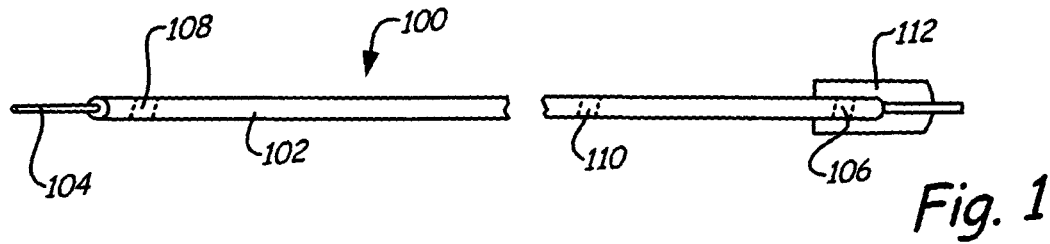
FIG. 1 is a perspective view of a tube with a corewire extending within the central lumen of the tube.

An integrated guiding device comprises a thin corewire and a small diameter tubing/catheter, e.g., a hypotube or polytube, that goes over the corewire with a torque coupler to couple the small diameter tubing to the corewire. The torque coupler provides considerable advantages with respect to delivery of the integrated guiding device while providing for desired longitudinal relative motion of the corewire and tube. The integrated guiding device can be used for the delivery of appropriate medical treatment devices and the like. In addition, the integrated guiding device can comprise the tube and corewire along with a functional medical component, such as an actuatable medical structure or the like, integrated into the integrated guiding device structure, as described further below for an embolism protection structure, which filters fluid flow to entrap emboli. The functional medical structure, for example, can be located near the distal end of the corewire. In particular, the longitudinal movement of the corewire with respect to the small tube provides for actuating features of a functional medical component coupled with the integrated guiding device, while the torque coupling provides excellent sterility for delivery of the devices. In some embodiments, for convenience the tube has the outer dimensions approximating a standard guidewire. If the tube has the outer dimensions of a standard guidewire, interventional devices such as balloons, stents and the like can be delivered over tube as with a standard guidewire or hypotube. Additional flexibility results from the ability to provide distant communication from the distal end to the proximal end through the relative longitudinal motion of the corewire and the tube.

The integrated guiding device generally comprises a thin corewire, a tube over the corewire and a torque coupling structure that couples torque on the tube with torque on the corewire, such as near or at the distal end of the corewire. In some embodiments of interest, by parsing the diameter of a standard guidewire into a thinner corewire and a small diameter tubing or tube, structure is introduced that can communicate between the proximal end and the distal end by longitudinally moving the corewire and the hypotube relative to each other. Thus, the integrated guiding device has a structure that can take advantage of these features with respect to manipulations at the distal end from the proximal end. At the same time, the outer surface of the tube can be used as a guide to introduce additional treatment devices that can be delivered over standard guidewires. However, to be effective, the corewire of the integrated guiding device should be positionable within the patient. To achieve this objective, generally torque has to be applicable to the distal end of the integrated device through the application of torque at the proximal end external to the patient such that the corewire can be manipulated by the physician/health care professional to guide the corewire to a specific location within the body. The integrated guiding device can be sufficiently flexible to follow branches of a patient's vascular system. The integrated guiding device facilitates guidance of the corewire and promotes design flexibility of the integrated device.

While in some embodiments the corewire and tube have especially thin cross sections, in other embodiments the corewire can have conventional thicknesses of a guidewire and the tube can have conventional dimensions of a catheter. However, for embodiments in which the corewire and tube have particularly thin cross sections, due to the extremely thin nature of the corewire, the wire can twist such that torque cannot be efficiently transferred from the distal end of the corewire to the proximal end of the corewire without the presence of the torque coupler. For any of the embodiments, to facilitate transfer of torque from the distal end to the proximal end, the corewire and tube can be coupled together to provide to torque transmittal, i.e., rotational communication, from the tube to the corewire.

The integrated guiding device generally comprises a torque coupling structure that couples torque on the tube with torque on the corewire. Due to the thicker profile of the tube, the corewire rotationally coupled to the tube can more effectively transmit torque from the proximal end of the device to the distal end of the corewire. Thus, a torque coupling structure is generally located near the distal end of the tube and the corewire. However, the torque coupling structure can extend along the entire length of the tube or any reasonable fraction thereof. With this structure, torque applied to the proximal end of the tube and/or corewire can result in efficient transfer of torque on the distal end of the corewire. In some embodiments, the integrated guiding device comprises one or more additional torque coupling structures, for example, near the proximal end of the tube and corewire and/or at or near the center of the tube.

Suitable torque couplers can provide rotational coupling between the tube and the corewire. In some embodiments, the torque coupling is always present, while in other embodiments the torque coupling is only present when the torque coupler is actuated. If the torque coupler is not always engaged, longitudinal motion between the tube and the corewire may or may not be possible when the torque coupler is engaged. In general, longitudinal motion between the tube and the corewire is possible at selected times. Thus, for embodiments in which the torque coupler is always engaged, longitudinal motion between the tube and the corewire is generally always available unless some other functional feature prevents the longitudinal motion at particular times.

Various structures can be used to provide the desired rotational coupling. For example, the tube can provide a key way that engages the corewire as a key. In other words, the corewire has structure that engages corresponding structure on the tube. This lack of circular symmetry of the corewire and inner surface of the tube provide the desired rotational coupling. This rotational engagement of the corewire and tube can be only over a portion of the length of the corewire, generally at least a portion of which is toward the distal end of the tube. Such a key way-key structure can provide the rotational coupling without preventing relative longitudinal motion of the corewire and tube, although the longitudinal motion may be restricted over a particular range. Specifically, by limiting the longitudinal extent of the torque coupler, the longitudinal motion of the corewire relative to the tube may be limited and/or the torque coupling may be limited to specific longitudinal alignments of the corewire and the tube. Several specific embodiments are described below.

In alternative embodiments, the rotational motion itself alters the structure to engage the rotational coupling. For example, in one embodiment below, a coil associated with the tube engages the corewire upon the application of rotational motion such that the tube becomes rotationally coupled to the corewire. Also, in other embodiments, threads on the tube and corewire can be engaged to rotationally couple the tube and the corewire. In additional embodiments, the rotational coupling may only be provided at select times. For example, a compressible section of the tube can be compressed to provide the desired rotational coupling at a selected time. Also, an electromagnetic coupling can be engaged at selected time to provide rotational coupling of the tube and the corewire. If the rotational coupling is engaged at select times, longitudinal motion may be restricted during these limited times while allowing relative longitudinal motion of the tube and corewire when the rotational coupling is not engaged.

The relative longitudinal motion of the corewire relative to the tube can provide for communication from the proximal end to the distal end of the integrated guiding device. In particular, this relative longitudinal motion can be used to actuate a medical device at or near the distal end of the integrated guiding device. A backend tool or pull element at the proximal end of the integrated guiding device can be used by the health care professional to control the movement of the corewire. Also, the pull element can resist undesired bending of the corewire for the portion that extends beyond the end of the tube. Embodiments of a pull element that have two stop points for an actuated and an unactuated position are presented below. The two stop points indicate the ends of the range of motion of the corewire relative to the tube. The use of locking stop points prevents the movement of the corewire at undesired times.

In some embodiment, it may be desirable to position the corewire at intermediate points between the limits of the range of positions. For example, for the deployment of a fiber-based embolism protection device, it may be desirable to actuate the device different amounts depending on the particular diameter of the vessel in which it is being deployed. In some embodiment, it may be desirable to position stably the corewire along a continuous range of positions. In some embodiments, this selectable degree of actuation can be used to obtain more consistent deployment of the device. A pull element can be marked appropriately to guide the desired degree of actuation while providing limits at both ends of the range of motion.

The continuous or intermediate placement of the corewire or corresponding actuation of the medical device can be achieved without losing control of the corewire through the introduction of friction between the corewire and the corresponding tube. While friction can be introduced in a range of ways into the system, a shape, such as a kink, bend or curve, with selected properties can introduce an effectively reproducible amount of friction into the motion of the corewire. Alternatively or additionally, the continuous deployment of the corewire can be accomplished with friction in a pull element, or a continuously variable locking feature in the pull element. Similarly, a ratchet style locking pull element can be similarly used to lock the pull wire at intermediate positions between the end stop points. At the selected intermediate or continuously adjustable position, the position of the corewire relative to the tube is stably positioned, i.e., effectively locked relative to any forces experience by the medical device deployed within a vessel of a patient that tend to move the corewire relative to the tube spontaneously. The amount of friction also generally is selected to be large enough to resist the compressive forces generated from sliding therapeutic devices over the tube.

To facilitate steering of the integrated guiding device, embodiments are described with a coil located near the distal end of the tube along a section of the tube with a reduced outer diameter. The portion of the tube with the coil has greater flexibility than the remaining portions of the tube. In alternative embodiments, the tube or other catheter device can have slots, such as transverse slots, cut along the tube toward the distal end of the device. The slotted portion can be placed at or near the distal end. Generally, the slotted portion is located in the distal half along the length of the tube/catheter. The number, size and position of the slots can be selected to provided the desired degree of flexibility of the tube or other medical catheter, although generally a relatively large number of slots are cut into the device. The slots may or may not cut through the material of the tube to the inner lumen. While the slotted tube is desirable for use in an integrated guiding device, other biological catheter can similarly benefit from this structure.

While an integrated guiding device as described herein can be conveniently used for the delivery of additional medical devices over the tube, one or more functional medical structures can be incorporated into the integrated guiding device. In particular, it can be desirable to interface the functional medical structures with both the corewire and the tube. By interfacing the functional medical structure to the corewire and the tube, the longitudinal motion of the corewire with respect to the tube can be used to send a signal to the functional medical structure from outside of the patient's body. Specifically, the longitudinal motion of the corewire and the tube can be used to actuate or de-actuate the functional medical structure. Suitable functional medical structures include, for example, embolism protection components.

In general, desirable embolism protection structures can be formed using filtering media with a three dimensional filtering matrix such as provided by a bundle of fibers. A fiber-based embolism protection component connected to an integrated guiding device is described further below. In this device, the fibers are attached at one end to the corewire and at the other end to the tube, e.g., a hypotube. The device can be deployed with the fibers stretched into a relatively low profile configuration. Upon longitudinal pulling the corewire proximal relative to the tube, the fibers flare outward to a deployed configuration in which the device can provide filtering within a patient's vessel. Reversal of the longitudinal motion of the corewire relative to the tube can stretch the fibers to a removal configuration. Additional embodiments of embolism protection devices are described in copending U.S. patent application Ser. No. 10/414,909 to Ogle, entitled "Embolism Protection Device," incorporated herein by reference. Aspiration can be applied during the removal of the device, as described further in copending U.S. patent application Ser. No. 10/854,920 filed May 27, 2004 to Galdonik et al., entitled "Emboli Filter Export System," incorporated herein by reference.

In some embodiments, the fiber-based embolism protection device comprises surface capillary fibers. Experiments indicate that devices formed with surface capillary fibers provide excellent filtering properties. Embolism protection devices with surface capillary fibers are described further in copending U.S. patent application Ser. No. 10/795,131 filed Mar. 6, 2004 to Galdonik et al., entitled "Fiber Based Embolism Protection Device," incorporated herein by reference. It has been discovered that the twisting of a fiber bundle, such as an SCF fiber bundle, in an embolism protection device can assist with keeping the fibers free of gaps during deployment and can result more consistent performance of the filter following deployment in a patient. Rotationally locking the tube to the corewire allow for the fiber bundle to be twisted and for the twist to be preserved through sterilization and final use of the device. In some embodiments, gentle heat can be added during the manufacturing process to impart a shape memory into the polymer, although heat is not required for consistent performance of the device or for elimination of gaps in the deployed fibers. In further additional or alternative embodiments, the fiber bundle can be twisted while the fibers are being deployed. This twisting during deployment within the patient results in even more consistent fiber placement within the deployed device.

The integrated guiding devices described herein can be used effectively to guide the corewire and associated medical devices through intricate pathways within the body. Specifically, devices can be guided into coronary arteries as well as along similar highly branched and curved pathways. The maneuverability has been confirmed for embodiments described below using animal studies and human model systems. The improved maneuverability has been confirmed in comparison with commercial systems that are available. Thus, the integrated guiding devices described herein can provide improved performance for a range of medical procedures involving less invasive intervention.

In summary, the integrated guiding devices described herein provide for very small diameter components with excellent maneuverability while maintaining desirable degrees of freedom. The integrated guiding devices used with integral medical structures and/or with associated medical devices delivered over the tube can be positioned precisely within the body with less effort while providing desired functionality by the ability to longitudinally move the corewire and the tube relative to each other. Thus, functionality can be maintained without sacrificing the ease of steering of the device to a selected location within a patient's body.

While the devices described herein are well designed for use in less invasive procedures, the devices can be incorporated into systems for use with respect to exposed vessels during surgery. The surgical system generally comprises a guide structure, such as an integrated guiding device as described herein, as well as a filter element and an aspiration catheter. The filter element can have a structure incorporating fibers, such as surface capillary fibers, in a bundle. The bundle of fibers can be connected to an integrated guiding device, for example, as described herein with the fibers attached to both the corewire and the corresponding over tube. In general, for surgical systems the guide structure can be significantly shorter than used for many minimally invasive procedures. An aspiration catheter can be used to collect emboli that may be released during retrieval of the filter. The aspiration catheter can have a short extent such that it can be mounted over the guide structure until used. A cannula can be similarly mounted over the guide structure for use to facilitate insertion of the filter and guide structure into the patient's vessel.

The surgical systems are well suited for use during carotid endartorectomy to block passage of emboli from flowing to the patient's brain. The surgical systems are also suitable, for example, for use in procedures involving the placement of vascular grafts, such as coronary artery bypass grafting, in which the graft is subject to anastamose through an incision as part of the procedure. However, more generally, the surgical systems can be used for any procedures Performed on an exposed vessel. The filter can be placed at an early stage of the procedure to prevent emboli from migrating down stream during the procedure and removed at the end of the procedure. The many advantages of the devices described herein can be taken exploited similarly in the surgical procedures. While generally the patient can be any mammal such as a domestic pet or farm animal, patients of particular interest are humans.

General Structure of the Integrated Guiding Device

In general, an integral guiding device comprises a corewire, a tube over the corewire, a torque coupler, and one or more optional, functional medical structures connected to the corewire and/or tube. The torque coupler provides coupling of rotational motion between the corewire and the tube, which may or may not be maintained at all times. An integrated guiding device, as described herein, is shown schematically in FIG. 1. Device 100 comprises tube 102, corewire 104, first torque coupler 106, second torque coupler 108, third torque coupler 110 and functional medical structure 112. The length of tube 102, e.g., a hypotube or a polytube, can generally be selected for the particular application. For example, for intervention in the aorta, the tube generally would have a length from about 190 cm (63 inches) to about 300 cm (106 inches). The cross section of the tube can be characterized by an inner diameter and an outer diameter. The inner diameter generally ranges from about 0.001 inches to about 0.01 inches, in further embodiment from about 0.003 inches to about 0.008 inches and in additional embodiments from about 0.005 inches to about 0.007 inches. The outer diameter generally ranges from about 0.04 inches to about 0.009 inches, in further embodiments from about 0.03 inches to about 0.010 inches, in additional embodiments from about 0.02 inches to about 0.011 inches and in other embodiments from about 0.015 inches to about 0.013 inches, with standard guidewire outer diameters being about 0.014 inches. The corewire has, a diameter just slightly less than the inner diameter of the tube by about 0.001 inches to about 0.003 inches. A person of ordinary skill in the art will recognize that additional ranges within the explicit ranges for the diameters are contemplated and are within the present disclosure.

In some embodiments, the corewire has a length such that the corewire extends past the distal end of the tube while extending also from the proximal end of the tube. Generally, the corewire, extends from the proximal end of the tube to provide for independent manipulation, of the corewire relative to the tube, especially for longitudinal movement and from the distal end for attachment to a medical device such as grippers or an embolism protection device. The proximal end of the corewire can have a gripper or the like that both facilitates gripping the proximal end of the corewire and simplifies longitudinal movement. The distal end can have one or more coils over the corewire to provide flexibility and radiopacity while maintaining overall diameter.

In general, the tube 102 and corewire 104 can be formed from one or more of various materials, such as polymers, metals and combinations thereof. The tube and corewire may or may not be formed from the same material. Suitable materials are generally biocompatible in that they are non-toxic, non-carcinogenic and blood compatible and do not induce hemolysis or a significant immunological response. Suitable biocompatible metals include, for example, titanium, cobalt, stainless steel, nickel, iron alloys, cobalt alloys, such as Elgiloy®, a cobalt-chromium-nickel alloy, MP35N, a nickel-cobalt-chromium-molybdenum alloy, and Nitinol®, a nickel-titanium alloy.

Suitable polymers include, for example, synthetic polymers as well as purified biological polymers and combinations thereof. Suitable synthetic polymers include, for example, polyamides (e.g., nylon), polyesters (e.g., polyethylene teraphthalate), polyacetals/polyketals, polyimide, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Based on desirable properties and experience in the medical device field, suitable synthetic polymers include, in particular, polyether ether ketones, polyacetals, polyamides (e.g., nylons), polyurethanes, polytetrafluoroethylene, polyester teraphthalate, polycarbonates, polysulfone and copolymers and mixtures thereof.

In other embodiments, the surface of the corewire, the inner surface of the tube, the outer surface of the tube, portions thereof or combinations thereof is coated with a friction reducing agent. Suitable friction reducing agents include, for example, suitable polymers, such as polytetrafluorethylene, i.e., Teflon® or a coating such as parylene. The coating of the corewire can facilitate relative longitudinal motion of the corewire relative to the tube.

The outside of tube 102 or corewire 104 or a portion thereof, such as a portion at or near the distal end, can have surface capillary fibers associated with the surface. The attachment of the surface capillary fibers generally depends on the material of the surface. For example, covalent bonding and/or adhesives can be used for the attachment. Surface capillary fibers have contoured surfaces with one or more surface capillaries along the length of the fiber or a portion thereof. The surface capillary fibers can moderate the character of fluid flow along the surface, such as reducing turbulence and can be used to effectively deliver bioactive agents in a controlled fashion. The use of surface capillary fibers in medical devices generally and catheters and associated articles is described further in copending U.S. patent application Ser. No. 10/781,503 to Ogle et al., filed on Feb. 18, 2004, entitled "Medical Article Incorporating Surface Capillary Fiber," incorporated herein by reference.

Torque couplers 106, 108, 110 generally provide at least temporary torque coupling without preventing at appropriate times relative longitudinal motion of the tube and the corewire. Various designs can accomplish this objective. In some embodiments, due to the very thin nature of the corewire, torque applied at the proximal end can fade as a result of twisting of the wire such that the amount of rotation at the distal end is less than desired relative to the rotation at the proximal end. The tube is also thin, and also may transfer torque poorly. However, by coupling the rotational motions of both members, the rotation of the distal end of the corewire can be controlled more precisely in the coupled system by rotating the tube at the proximal end. The torque coupler(s) couples the rotational motions of the two components.

In particular, the torque couplers can provide at least temporary angular engagement of the tube with the corewire. This engagement can be constrained to localized regions such as a region at or near the distal end of the tube, a region at or near the proximal end of the tube and/or a region between the locations at or near the respective ends of the tube. In particular, it can be desirable to have rotational coupling between the tube and the corewire within twenty centimeters of the distal end of the wire and in some embodiments within about four centimeters from the distal end of the tube. Generally, it is advantageous to couple the tube and corewire in a distal-most region if the desired goal is efficient transfer of torque to the distal tip. In some embodiments the rotational coupling extends along the entire length of the tube.

Several specific embodiments are depicted in the Figures. In some embodiments, tube 102 and corewire 104 comprise a key way with a matched key that engage each other to rotationally restrict the movement of corewire 104 within tube 102. In these embodiments, the corewire does not have a circular cross section, at least not along its entire length. A variety of different structures are possible for the key way/key combinations with three embodiments shown in FIGS. 2, 3 and 5.

Figure 2:
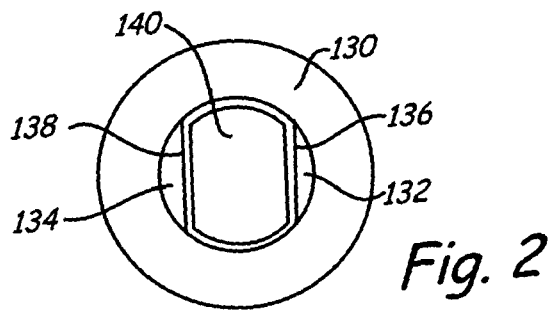
FIG. 2 is a sectional view of a first embodiment of a torque coupler with a key way-key structure rotationally connecting the tube and corewire of FIG. 1.
Figure 3:
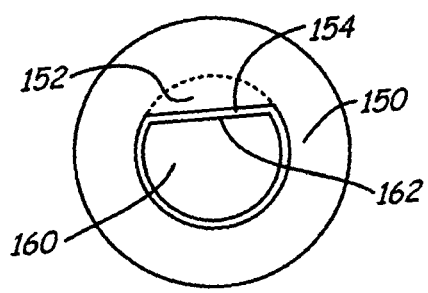
FIG. 3 is a sectional view of an alternative embodiment of a torque coupler with a key way-key structure rotationally connecting the tube and corewire of FIG. 1.

Referring to FIG. 2, a tube 130 has two key ways portions 132, 134 along the inner diameter that break the circular symmetry of the inner diameter and forms an asymmetric key way that engages the asymmetrical corewire as the key. In particular, key way portions 132, 134, respectively, have flat surfaces 136, 138 that engage corewire 140. Corewire 140 has a cross section that corresponds with the interior of tube 130. Specifically, corewire 140 has flat surfaces 142, 144 that engage flat surfaces 136, 138, respectively. An alternative embodiment is shown in FIG. 3. As depicted in FIG. 3, tube 150 has one key way portion 152 forming an engaging surface 154. Corewire 160 fits within the inner lumen of tube 150. Corewire 160 has a corresponding engaging surface 162 that breaks the circular symmetry of the cross section of the corewire and that allows the corewire to function as a key. Engaging surface 162 engages surface 154 of tube 150. Other embodiments are similarly possible, for example with three of more key way portions projecting into the inner lumen of the tube, in addition, to the one and two key way portion embodiments of FIGS. 2 and 3. Also, the shape of the engaging surface does not need to be flat as long as the engaging surfaces of the tube and the corewire rotationally couple the tube and the corewire.

Figure 4:
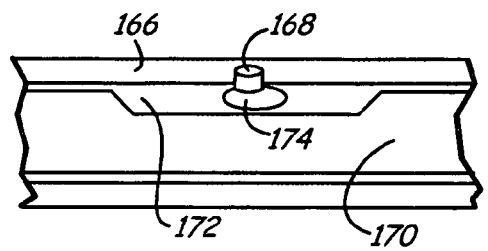
FIG. 4 is fragmentary, sectional side view of tube and corewire with a port opening into the tube adjacent a key in the corewire that forms a mold for forming a key way associated with the tube.

The phantom lines in FIGS. 2 and 3 indicate that the key ways may or may not be formed from the same material as the remaining portions of the tube. The key ways of the tube can be integrally formed into the tube or formed within the tube, for example, with a polymer such as an epoxy. For example, to form the key ways of FIGS. 2 and 3, an adhesive or polymer can be injected into the lumen of the tube through a port or the like. The port can be formed by laser cutting or other suitable drilling process. Upon curing, the adhesive/polymer forms the key way. The corewire can be coated with a non-stick coating, such as polytetrafluoroethylene (Teflon®) or parylene. Referring to FIG. 4, tube 166 has a port 168. Wire 170 has a key 172 that forms a mold for the adhesive/polymer 174.

Figure 5:
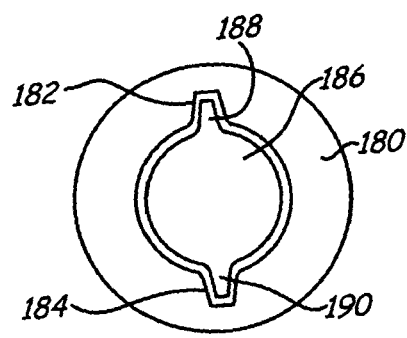
FIG. 5 is a sectional view of a second alternative embodiment of a torque coupler with a key way-key structure rotationally connecting the tube and corewire of FIG. 1.

As shown in FIGS. 2 and 3, the tube key way extends into the interior lumen of the tube. In additional embodiments, the tube key way more resembles a recess or indentation, and one or more projecting key elements from the corewire extends into the key way. As shown in FIG. 5, an embodiment has a tube 180 with notches 182, 184 that act as key ways for engaging corewire 186. Corewire 186 has two ridges or teeth 188, 190 that fit within notches 182, 184. The shape, size and other features of notches 182, 184 and ridges 188, 190 can be selected based on particular design considerations by a person of ordinary skill with the constraint that the ridges fit within the notches. Similarly, the number of notches and ridges can be one, two, three, four or more as appropriate. The notches and ridges can be formed along with the respective tube and corewire, for example, by extrusion, or they can be formed subsequently, for example, by machining, molding or adhering the appropriate structures.

The projecting key ways of FIGS. 2 and 3 can be combined with notch key ways of FIG. 5 in a single embodiment if desired. Similarly, the distinction may be blurred in some embodiments whether or not the key way is a projection into the lumen or a notch from the lumen into the tube structure. The significant feature is that a key way and key are mated such that the tube rotationally engages the corewire.

As shown in FIGS. 2, 3 and 5, the tube and corewire rotationally engage each other with a key way-key relationship that does not inhibit relative longitudinal motion of the tube and corewire along the length of the elements. This relationship is based on the assumption that the key way extends along the entire length of the tube. Thus, torque can be transmitted from the tube to the corewire without interfering with the capability to move longitudinally the tube relative to the corewire. However, the longitudinal dimension of the key way and/or the corresponding key structure of the corewire generally can be along the entire length of the tube and/or the corewire or only a portion of the length. For example, the key way and key can be limited to a location at or near the distal, at or near the proximal end and/or at one or more locations more central to the tube or corewire structures.

Depending on the design of the key and key way, limiting the key way to only a portion of the length of the device can have various effects. In some embodiments, this localization can result in the torque coupling at only corresponding longitudinal positions of the corewire and tube with free rotation at other locations. In other embodiments, a notch in the tube can be localized within a key way on the corewire to limit the longitudinal motion of the corewire relative to the tube. A specific embodiment with this configuration is described in detail below. A variation of this embodiment with restricted longitudinal motion is described below with torque coupling in some longitudinal relationships and rotational freedom in other longitudinal relationships. For the deployment of a fiber-based embolism protection device, it can be desirable to rotate the fiber bundle while deploying the fibers from a low profile configuration to a configuration with the fibers extending across the vessel lumen. The amount of rotation generally is at least about 15 degrees, in further embodiments from about 45 degrees to about 450 degrees and in other embodiments from about 90 degrees to about 405 degrees. A person of ordinary skill in the art will recognize that additional ranges of rotation are contemplated and are within the present disclosure.

If the key way/key, structures do not extend along the entire length, the projecting structure, whether the key way or the key, generally extends for a shorter longitudinal length such that the interference of the key with the tube away from the key way does not undesirably interfere with the longitudinal degree of movement of the corewire relative to the tube. If the key way does not extend along the entire length of the tube, the relative longitudinal motion of the tube relative to the corewire may be limited. In particular, the projecting structure generally can only traverse within the extent of the corresponding indented structure. However, some limitation on the longitudinal motion may be desirable since in operation only a limited amount of longitudinal motion can provide the desired functionality while providing additional control of the limits of the movement.

If the key way and key extend along the entire length of the tube and corewire, the corewire can be inserted within the tube after they are formed. However, if the key way and key only extend over a portion of the length of the components, generally some of the structure is formed following insertion of the corewire into the tube. An example of this is described in more detail below.

Figure 6:
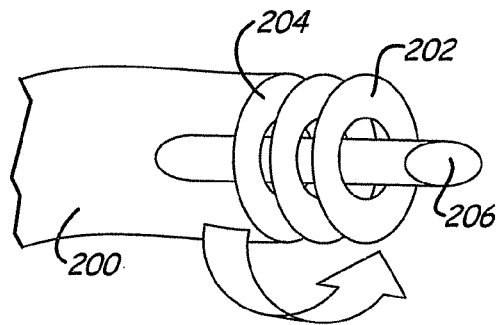
FIG. 6 is a schematic, fragmentary perspective view of a torque coupler with a coil at the end of the tube of FIG. 1 for rotational coupling with the corewire.
Figure 7:
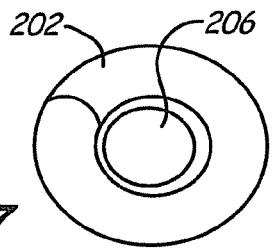
FIG. 7 is a sectional view of the torque coupler of FIG. 6 depicting the coil surrounding the corewire wherein they are disengaged.
Figure 8:
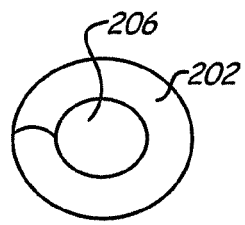
FIG. 8 is a sectional view of the torque coupler of FIG. 6 depicting the coil engaged with the corewire.

Another embodiment of a torque coupler is shown schematically in FIG. 6. As shown in FIG. 6, tube 200 has a coil 202 located at its distal end 204. Coil 202 extends over corewire 206. In its relaxed state, corewire 206 can move freely within coil 202, as shown in FIG. 7. However, upon rotation in the appropriate direction, coil 202 can tighten onto corewire 206 such that motion of the tube is coupled to corewire 206, as shown in FIG. 8. Thus, torque can be applied to the distal end of corewire 206 by applying torque to tube 200. Coil 202 can be formed from appropriate spring metals or other material. A person of ordinary skill in the art can select the dimensions and elasticity of the coil to yield desired degrees of coupling between the coil and the corewire. Using this embodiment, temporary coupling can be provided to rotationally couple the tube and the corewire while providing for relative longitudinal motion of the tube and corewire at other times.

Figure 9:
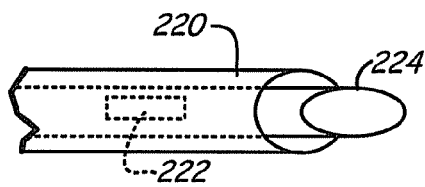
FIG. 9 is a schematic, fragmentary perspective view of a torque coupled based on a compression section.

In a further embodiment, tube 220 has a compressible section 222, as shown in FIG. 9. Corewire 224 extends within the internal lumen of tube 220. Compressible section 222 generally has an elasticity such that compressible section 222 can be pressed with a reasonable force against corewire 224 to couple tube 220 to corewire 224. Compressible section 222 can be formed, for example, by machining away a section of tube 220 and adding a plug of an appropriate material, such as an elastomeric polymer. An appropriate seal can be formed to prevent leakage of liquid at the compressible section. Thus, tube 220 and corewire 224 can be selectively coupled to provide for rotational coupling when desired and uncoupled when desired to allow for relative longitudinal motion. Compressible section 222 can be placed near the proximal end of the tube such that the compressible section can be engaged by a health care professional, such as a physician, during a procedure using the tube and corewire. In some embodiments, the compressible section is engaged by hand by pressing on the compressible section. This torque coupling element with a compressible section can be combined with other torque coupling elements, such as a torque coupling element at or near the distal end of the tube, for example, the types of torque coupling elements described above.

Figure 10:
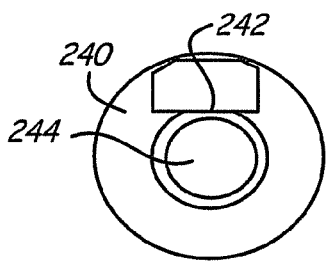
FIG. 10 is a sectional view of a torque coupler based on threads along the inside of the tube and threads on the outside of the corewire in which the threads are not engaged.
Figure 11:
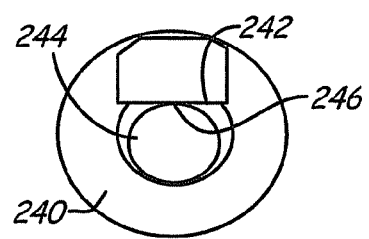
FIG. 11 is a sectional view of the torque coupler of FIG. 10 in which the threads are engaged.

In a further embodiment, the inner surface of the tube and the outer surface of the corewire have threads at a location along the length of the components. Rotation of the tube relative to the corewire can engage the threads and rotationally couple the tube to the corewire, while disengagement of the threads can allow for relative longitudinal movement of the tube and the corewire. Referring to FIG. 10, the cross section of a tube 240 with threads 242 is depicted with a threaded corewire 244 within the inner lumen of tube 240 with the threads disengaged. Referring to FIG. 11, threads 244 are shown engaging threads 246 of corewire 244. Threads 242 and 246 can be formed, for example, using standard approaches in the art. The threaded sections can be located at or near the distal end of the tube and corresponding portion of the corewire, although the threaded section or additional threaded sections can be placed at other locations along the length of the tube and corewire. While the presence of threads my limit the longitudinal movement of the tube and the corewire, for example, restricting motion in one direction, this may be adequate for many applications.

Figure 12:
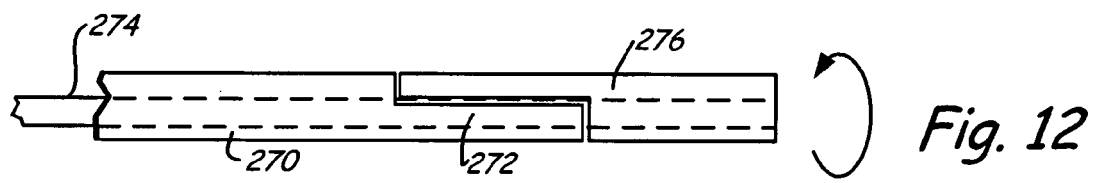
FIG. 12 is a side view of an alternative embodiment of a torque coupler with elements of the torque coupler attached, respectively, at the end of the tube and the corewire.
Figure 13:
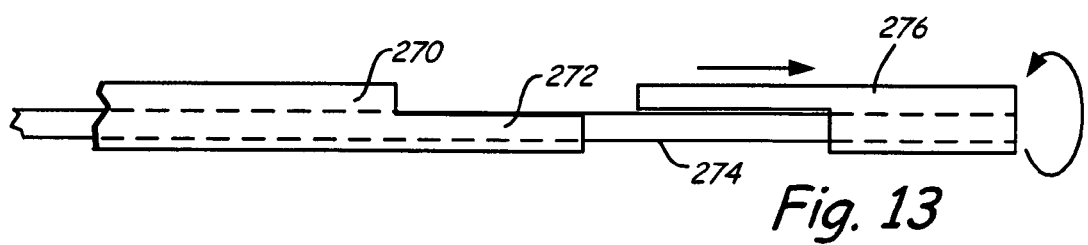
FIG. 13 is a side view of the torque coupler of FIG. 12 in which the torque coupler elements are disengaged.

Another embodiment of a torque coupler is shown in FIGS. 12 and 13. Tube 270 has a first coupling element 272 at its distal end. Corewire 274 has a second coupling element 276 at its distal end. As depicted in FIG. 12, first coupling element 272 engages second coupling element 276 to rotationally couple tube 270 with corewire 274. As depicted in FIG. 13, corewire 274 is moved toward the right relative to tube 270 to disengage first coupling element 272 and second coupling element 276 such that tube 270 and corewire 274 are not rotationally coupled.

Figure 14:
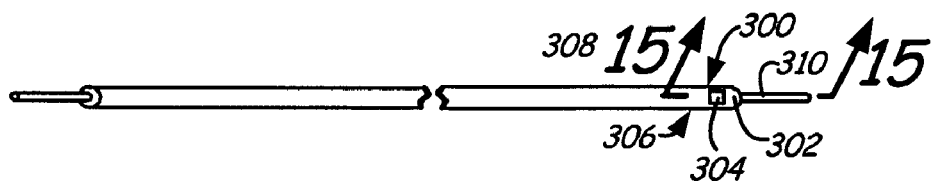
FIG. 14 is a side view of an integrated guiding device with a torque coupler based on electrostatic attraction.
Figure 15:
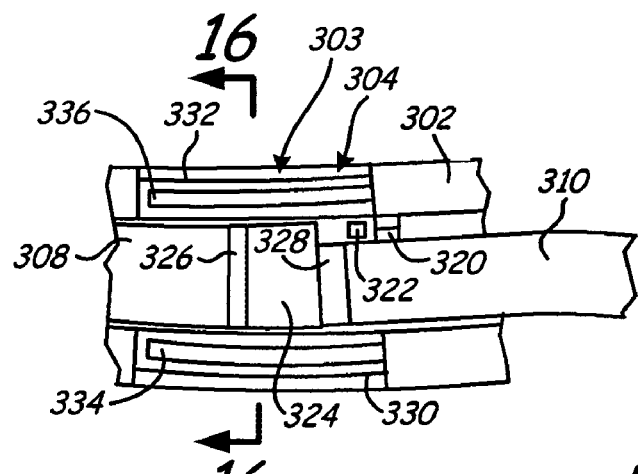
FIG. 15 is an expanded, sectional view of the torque coupler of FIG. 14 taken along line 15-15 of FIG. 14.

The torque coupling can also be controlled electromagnetically. A small battery can be placed near the distal end of the tube to power the coupling. Various electromagnetic couplings are possible to generate the torque coupling. An embodiment based on electrostatic attraction is shown in FIG. 14. Torque coupler 300 comprises a battery 302, a switch 304 and electrostatic coupler 306. Battery 302 is mounted on tube 308 and has a hole to provide for passage of corewire 310. Various designs of a switch can be used. Embodiments of switch 304 and electrostatic coupler 306 are shown in FIG. 15. In this embodiment, switch 304 is closed by pushing corewire 310 distal, i.e., toward the right in the orientation of FIG. 14, relative to tube 308, such that longitudinal movement of the corewire proximal relative to the tube is unobstructed by the switch and does not couple the torques. Switch 304 comprises a lead 320 connected to a first terminal of battery 302 and an optional spring 322 comprising a bend section of elastic metal.

Figure 16:
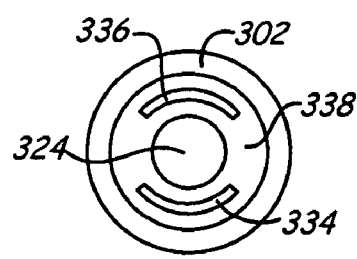
FIG. 16 is an expanded, sectional view of the torque coupler of FIG. 14 taken along line 16-16 of FIG. 15.

Upon translating corewire 310 toward the right in the configuration of FIG. 15, corewire section 324 contacts lead 320 while deflecting spring 322. Corewire section 324 comprises an electrically conductive material, such as a metal and is surrounded by electrically insulating sections 326, 328. Electrostatic coupler 306 comprises deformable sections 330, 332 on tube 308 and electrically conductive sections 334, 336 that are connected to the opposite terminal of battery as lead 320. Electrically insulating material 338, such as an electrically insulating polymer, surrounds sections 334, 336 to prevent shorting of the battery due to contact between sections 334, 336 and corewire section 324. The sectional view of electrostatic coupler is depicted in FIG. 16. When the switch is closed, sections 334, 336 and corewire section 324 charge with opposite charges, like a capacitor such that deformable sections 330, 332 deflect to grip corewire 310 due to electrostatic attraction. Spring 322 can be used to open the switch when the corewire is not being pushed to close the switch.

The longitudinal freedom of motion of the tube with respect to the corewire provides for communication between the proximal and distal ends of the devices. Thus, the relative motion of the components can be used to actuate functional structures built into the distal end of the combined device. Functional medical components, such as actuatable medical treatment structures, are described in the following.

While the corewire and tube are intended to have at least limited, relative longitudinal movement, the longitudinal movement of the corewire within the tube should be controllable. Specifically, in some embodiments, the relative motion of the corewire and the tube provide for functional actuation of an associated medical device, such as an embolism protection devices as described below. The medical professional using the device generally controls the actuation of the corewire to achieve a specific medical interaction such that uncontrolled or accidental movement of the corewire may frustrate the intended purpose of the medical device and in some cases could be dangerous to the patient.

To control relative motion of the corewire and tube, a backend tool or pull element can be used that constrains the relative position of the corewire and tube. Specific embodiments of locking pull elements are described further below. However, for alternative or additional embodiments, control of the relative motion of the corewire and tube can be provided sufficiently or at least in part through friction between the corewire and tube. A pull element can control the limits of the motion of the corewire relative to the tube. Friction can provide desired control to the health care professional while reducing or eliminating spontaneous and accidental movement of the corewire relative to the tube.

Figure 17:
FIG. 17 is a side view of a corewire with a bend to provide for friction between the corewire and a tube.

Friction can be provided by roughening all or a portion of the corewire and/or all or a portion of the inner surface of the tube. However, providing a shape, such as a kink, bend or curve, in the corewire can provide consistent results with a smooth operation from the view point of the feel to the health care professional controlling the device. An example of a curved corewire is shown in FIG. 17. Specifically, corewire 350 has a bend 352. Bend 352 provided friction through contact with the inner surface of a corresponding tube. In general, bend 352 is positioned to not interfere with a torque coupler or other functional portion of the device. As shown in FIG. 17, bend 352 has two deflected bumps, although a single bump or more than two bumps can be used to provide the desired degree of friction. Also, friction can be provided by more than one bend. Similarly, the amount of deflection of the bump can be selected to provide the desired degree of friction. The amount of friction can depend on the elasticity of the material used to form the corewire. Bends can be formed with a suitable fixture to form a reproducible shape.

The use of friction to constrain the longitudinal movement of the corewire provides for continuous activation of a device controlled with movement of the corewire. For example, an embolism protection device can be actuated to different amounts depending on the amount of movement of the corewire. So for the fiber based embolism protection devices described herein, it may be desirable to expand the fibers outward a greater degree for slightly larger vessels in contrast with deployment in smaller vessels. Of course, a particular device can be designed for use in vessels over a range of sizes, but additional control of the function can be provided with continuous actuation to provide for a range of deployment for vessels within the acceptable ranges. This control can provide more consistent performance of the associated device. To similarly provide continuous control of activation, friction can be provided within the backend tool itself and/or the backend tool can have a continuously adjustable locking feature, as described below.

Improved Catheter/Medical Tube Design

Slots can be used to increase the flexibility of a catheter, other medical tube/hypotube or a tube of an integrated guiding device, as described herein. In some embodiments, the slots are oriented with a direction having a transverse component to the orientation. In general, it may be desirable to have different flexibilities at different locations along a catheter or other medical tube. Specifically, it can be desirable to have increased flexibility toward the distal end of the catheter for steering of the device and other similar control aspects. As shown below, a coil is placed along the distal end of a tube used in an integrated guiding device to provide for greater flexibility near the distal end. However, the placement of slots, such as transverse slots, offer more consistent performance and simpler construction as an alternative to a coil. The use of a coil to provide for transitioning flexibility of a catheter is described, for example, in U.S. Pat. No. 6,273,879 to Keith et al., entitled "Balloon Catheter With Distal Guide Wire Lumen," incorporated herein by reference. However, the use of slots provides increased flexibility generally without significantly increasing the stretch and compression of the structure in the region of increased flexibility. By reducing stretch and compression, there is a corresponding reduction in recoil associated with actuation of a medical device, such as an embolism protection device, associated with the tube.

A selected degree of flexibility is introduced by one or more slots. In some embodiments, the slots have at lease a portion of their orientation along a transverse direction. A slot is a cut through or into the material of the catheter/tube. The catheter/tube generally has an axis that aligns the longitudinal direction of the tube when the tube is placed in a linear configuration. The transverse direction is perpendicular to the longitudinal axis such that slots with a transverse component of their orientation are not aligned only along an axial direction. However, in general, a slot can have any shape and not just a narrow elongated shape, although a thin elongated shape can be convenient. The angular extent of a slot along the circumference can be evaluated from a projection of the slot onto a transverse plane. For specificity, a slot with a transverse component of its orientation can be described herein by a slot that extends at least about 25 degrees around the circumference of the catheter/tube, in additional embodiments at least about 30 degrees and in further embodiments from about 45 degrees to about 330 degrees. In some embodiments, the slot extends at least about 90 degrees and may extend from about 180 degrees to about 315 degrees. A person of ordinary skill in the art will recognize that additional ranges of transverse orientation within the explicit ranges above are contemplated and are within the present disclosure. The remaining portion of the catheter/tube not cut should provide sufficient mechanical strength such that the catheter/tube does not break.

Figure 18:
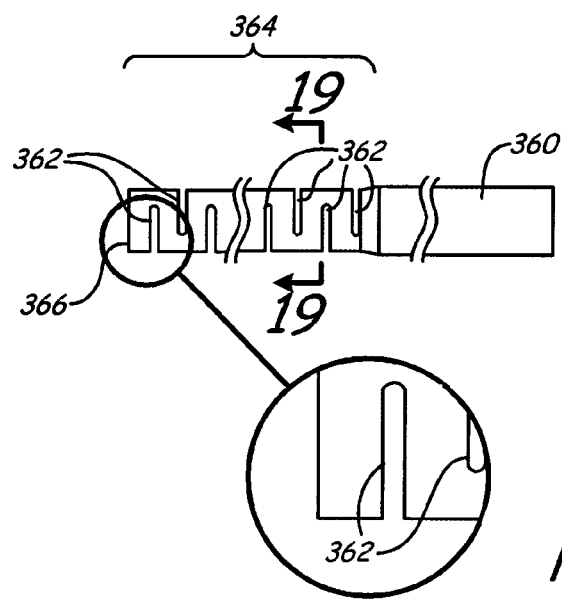
FIG. 18 is a side view of a catheter/tube with a slotted portion with a fragmentary exploded view shown in the insert.
Figure 19:
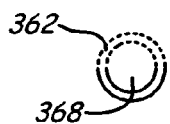
FIG. 19 is a sectional plan view of the catheter/tube of FIG. 18 taken along line 19-19 of FIG. 18.
Figure 20:
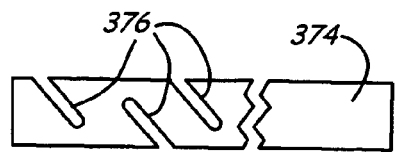
FIG. 20 is a side, view of an alternative embodiment of a catheter/tube with a slotted portion.

An embodiment of a catheter/tube with a plurality of transverse slots is shown in FIG. 18. In this embodiment of a catheter/tube 360, a plurality of slots 362 are located in a slotted region 364 at the distal end 366 of catheter/tube 360. Slotted region 364 is tapered with respect to outer diameter relative to the remaining section of catheter/tube 360. An expanded view of one slot 362 and portion of a second slot is shown in the insert for FIG. 18. Slots 362 alternate in position with adjacent cuts being mirror images of each other through a plane passing through the central axis. Slots 362 have a transverse orientation perpendicular to the central axis of the tube. Slots 362 roughly involve cuts through 240 degrees of the circumference leaving roughly 120 degrees uncut. A sectional view along one slot 362 is depicted in FIG. 19 showing an inner lumen 368. An alternative embodiment of a slotted catheter/tube is shown in FIG. 20 in which catheter/tube 374 has slots 376 that have an orientation with both significant transverse and a longitudinal components. In other words, slots 376 are oriented along a non-perpendicular angle to the axis of the tube. In one embodiment, the slots have a width of 0.0008 inches with a semi-circular edge at the end of the slot and a 0.0005 inch spacing between adjacent slots, although other parameters can be used as desired.

The dimensions of the slotted region can be selected to yield desired properties. For a standard 70 inch catheter, the slotted region can be, for example, from 5 to 15 inches, and in other embodiments from 8 to 12 inches. A person of ordinary skill in the art will recognize that additional ranges of slotted region lengths within the explicit ranges are contemplated and are within the present disclosure. Generally, the slotted portion is located within the distal half along the length of the catheter/tube. The number of slots can range from one to a large number to provide desired degrees of flexibility. Similarly, the catheter/tube can have an unslotted portion distal to the slotted portion, for example, if useful for use with an associated medical device. Slotted portion 364 may or may not be located along a taper in outer diameter with FIG. 18 depicting a tapered embodiment and FIG. 20 depicting a non-tapered embodiment. As shown in FIG. 18, the slots are equally spaced and equivalent in size, but other spacing arrangements and variations in size of different slots can be used to achieve desired flexibility.

Figure 21:
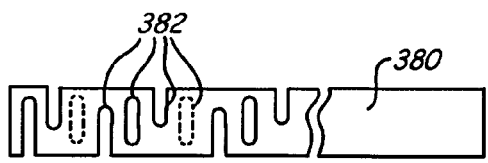
FIG. 21 is a side view another alternative embodiment of a catheter/tube with a slotted portion.
Figure 22:
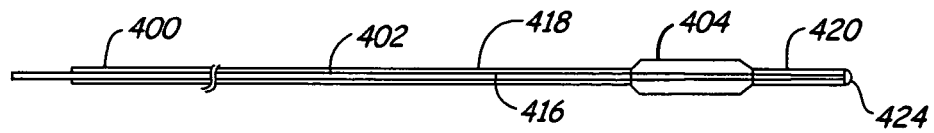
FIG. 22 is a sectional side view of a particular embodiment of an integrated embolism protection device and delivery tool.

Due to the presence of two slot orientations that are mirror images of each other, catheter/tube 360 of FIG. 18 has flexibility primarily in one plane. Additional three dimensional flexibility, if desired, can be introduced by including slots in additional orientations. For example, as shown in FIG. 21, catheter/tube 380 have slots 382 with four different orientations. These four configurations are rotated 90 degrees along the axis of the tube relative to other configurations. In general, a single orientation, two orientations, three orientations, four orientations, five orientations, six orientations or more orientations are possible to provide a desired degree and direction of flexibility.

While the catheter/tube, in principle, can be cast with the desired slots, in general convenient approaches involve the formation of the slots after the basic structure of the catheter/tube is formed. The slots can be cut into the catheter/tube using any practical approach. Suitable cutting techniques include, for example, mechanical cutting, electrostatic discharge machining (EDM), cutting with high pressure fluids, chemical etching and laser cutting. Laser cutting can be particularly efficient for the formation of a significant number of precision cuts using automated control, especially cuts that penetrate through the catheter/tube to the inner lumen. Etching may be particularly effective to form slots that do not penetrate through the material of the catheter/tube.

Functional Medical Components For Use With Integrated Guiding Device

In general, a functional medical component can be combined with an integrated guiding device. This can be particularly useful for an actuatable medical structure that can be actuated through the relative longitudinal motion of the corewire and the tube. Generally, this actuatable structure is located at or near the distal end of the integrated guiding device with corresponding actuation at the distal end of the device. For example, small grippers or fastener applicators can be placed at the end of the device. Suitable designs for a gripper and/or a fastener applicator that can be actuated with the relative motion of the corewire and the tube are described, for example, in U.S. Pat. No. 6,165,183 to Kuehn et al., entitled "Mitral And Tricuspid Valve Repair," incorporated herein by reference.

In addition, the functional medical component can be an embolism protection structure. Embolism protection structures of particular interest include, for example, fiber based embolism protection structures. As noted above, fibers with surface capillary fibers can be effectively used in embolism protection devices. In some embodiments, an embolism protection structure is placed at the distal end of the integrated guiding device. Relative motion of the corewire and the tube can be used to deploy the embolism protection structure from a confined narrow profile configuration for delivery to a deployed configuration at which the embolism protection structure is expanded within the vessel. The actuation, which is generated by the longitudinal motion of the tube relative to the corewire, can release the embolism protection structure from a constrained environments, as described further in U.S. patent application Ser. No. 10/414,909 to Ogle, entitled "Embolism Protection Device," incorporated herein by reference, or can directly drive a reconfiguration of the device into a form that filters the lumen of the vessel, as described further in U.S. Provisional Patent Application Ser. No. 60/489,044 to Ogle et al., entitled "Embolism Protection System," incorporated herein by reference.

Figure 23:
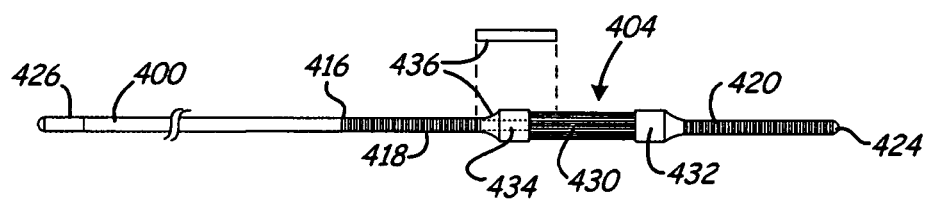
FIG. 23 is a side view of the integrated device of FIG. 22.
Figure 24:
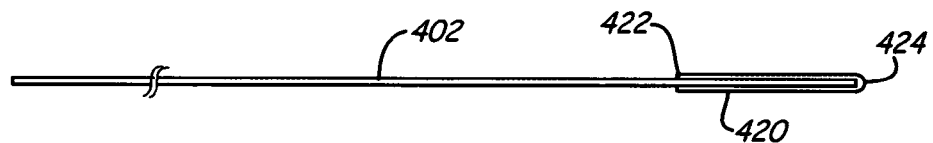
FIG. 24 is a side view of the corewire of the integrated device of FIG. 22.

One specific embodiment is shown in FIGS. 22-25. In this embodiment, the integrated guiding device comprises a tube 400, a corewire 402, and an embolism protection structure 404. Referring to the sectional view in FIG. 22 and the side view in FIG. 23, tube 400 has a tapered section 416 at its distal end that mimics the taper on a conventional corewire. A wire coil 418 is located over the tapered section 416. Corewire 402 is covered with a coil 420 at its distal end, as shown in FIG. 24. Coil 420 is connected with solder 422 and a weld 424, although other attachment approaches can be used. Tube 400, corewire 402, wire coil 418, coil 420 and grip 426 can all be formed from stainless steel, although other suitable materials can be used.

Figure 25:
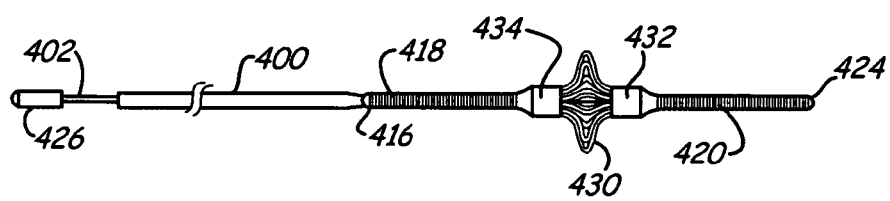
FIG. 25 is a side view of the device of FIG. 22 following expansion of the embolism protection device.

In this embodiment, embolism protection device 404 comprises a bundle of SCF fibers 430 attached at first attachment 432 and second attachment 434, as shown in FIGS. 23 and 25. A 0.1 inch long tube 436, which can be formed from polyimide polymer, is located within the second attachment 434 with corewire 402 extending within the tube. The fibers are swaged/crimped at the two attachments 432, 434 to a diameter of 0.033 inches with radio-opaque bands. After crimping, the fiber bundles are bonded at each end with an adhesive, such as cyanoacrylate.

The number of fibers in the bundle generally depends on the desired degree of filtration as well as the thickness of the fibers. In general, the number of fibers can be range from at least 10 fibers, in further embodiments from 25 fibers to 1,000,000 fibers, in other embodiments from 50 fibers to 10,000 fibers and in additional embodiments, from 100 fibers to 5,000 fibers. The length of the fibers can be selected based on the size of the corresponding vessel. When deployed, the centers of the fibers are projected across the lumen of the vessel. Thus, the unconstrained length of the fibers between attachment structures 432, 434 should be at least double the radius of the vessel. In some embodiments relating to the use of a plurality of fibers to expand within the lumen of a patient's vessel, it is generally appropriate to use fibers that have a length from about 2.2 to about 10 times the vessel radius, in some embodiments from about 2.4 to about 5 times the vessel radius and in further embodiments from about 2.6 to about 4 times the vessel radius. For placement in a human vessel, the fibers generally have a length from about 0.5 mm to about 100 mm, in other embodiments from about 1 mm to about 25 mm, and in further embodiments from about 2 mm to about 15 mm. A person of ordinary skill in the art will recognize that additional ranges of fiber numbers and fiber length within the explicit ranges are contemplated and are within the present disclosure.

As used herein, SCF fibers refer broadly to fibers having channels or capillaries along the surface running generally along the length of the fiber or a portion thereof. Fibers have their usual meaning as structures with a length that is significantly larger than the dimensions along a cross section perpendicular to the length. The capillaries can run along substantially the entire length or a fraction thereof. Due to the presence of the capillaries, a cross section through the fiber at the capillary(ies) has a shape with an edge having changing curvatures.

SCF fibers for use in the medical devices are generally formed from biocompatible polymers. SCF fibers can be fabricated from synthetic polymers as well as purified biological polymers and combinations thereof. Suitable synthetic polymers include, for example, polyamides (e.g., nylon), polyesters (e.g., polyethylene teraphthalate), polyacetals/polyketals, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Based on desirable properties and experience in the medical device field, suitable synthetic polymers include, in particular, polyether ether ketones, polyacetals, polyamides (e.g., nylons), polyurethanes, polytetrafluoroethylene, polyester teraphthalate, polycarbonates, polysulfone and copolymers and mixtures thereof.

Bioresorbable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly(hydroxy butyrate), and similar copolymers. Based on experience in the medical field, suitable resorbable polymers include, in particular, polylactic acid, polyglycolic acid, and copolymers and mixtures thereof.

Appropriate polymers also include biological polymers. Biological polymers can be naturally occurring or produced in vitro by fermentation and the like. Suitable biological polymers include, without limitation, collagen, elastin, silk, keratin, gelatin, polyamino acids, cat gut sutures, polysaccharides (e.g., cellulose and starch) and mixtures thereof. Biological polymers generally are bioresorbable. Purified biological polymers can be appropriately formed into a polymer material for further processing into fibers.

The properties of the surface channels and the corresponding cross-section of the fiber generally depends on the process used to form the fibers. U.S. Pat. No. 4,842,792 to Bagrodia et al., entitled "Drafting Process For Preparing A Modified Polyester Fiber," incorporated herein by reference, describes one approach for forming a fiber with a continuous surface "groove" that runs along the length of the fiber. The process in the '792 patent forms the groove starting from a conventional fiber. Another form of shaped fibers is described in U.S. Pat. No. 5,277,976 to Hogle et al., entitled "Oriented Profile Fibers," incorporated herein by reference. Other shaped fibers notches or channels are described in U.S. Pat. No. 5,458,963 to Meirowitz et al., entitled "Nonwoven Web Containing Shaped Fibers," incorporated herein by reference. Fiber with fairly complex surface channel geometry are described in U.S. Pat. No. 5,972,505 to Phillips et al., entitled "Fibers Capable Of Spontaneously Transporting Fluids," incorporated herein by reference. A further approach for forming a fiber with surface capillaries is described in U.S. Pat. No. 5,200,248 to Thompson et al. (hereinafter the '248 patent), entitled "Open Capillary Channel Structures, Improved Process For Making Capillary Channel Structures, And Extrusion Die For Use Therein," incorporated herein by reference. The Background section of the '248 patent additionally references a variety of alternative embodiments of approaches for forming fibers with surface channels or capillaries. Any of these approaches can be used. However, the fibers formed by the process of the '248 patent itself have desirable characteristics and versatility.

As with the fiber length, the thickness of the fibers can be selected appropriately for the particular use of the fiber. Fiber thickness can be measures in several ways. As described in the previous paragraph, the radius of the fiber can be roughly estimated from the assumption of a circular cross section. Alternatively, one can define an average diameter by taking an average cross section and then averaging the length of segments through the center of the cross section that intersect the circumference of the cross section. Also, calipers can be used to measure thickness, which can be averaged to obtain a value of the diameter. These various approaches at estimating the radius or diameter generally give values of roughly the same magnitude. Also, in the fiber field, a pragmatic way has been developed to characterize fiber thickness without the need to resort to magnification of the fibers. Thus, fiber thickness can be measured in units of denier. Deniers correspond to the number of grams per 9,000 meters of yarn with a larger value corresponding to a thicker fiber. In some embodiments, suitable fibers have diameters from 50 microns to about 5 millimeter, in further embodiments from about 100 microns to about 2 millimeters, and in additional embodiments from about 150 microns to about 1 millimeter. As measured in denier, SCF fibers can have sizes ranging from about 0.1 denier to about 1000 denier in size, in additional embodiments from about 0.5 denier to about 250 denier, in some embodiments from about 1.0 denier to about 200 denier, in other embodiments from about 2.0 denier to about 100 denier and in further embodiments from about 3.0 denier to about 50 denier. A person of ordinary skill in the art will recognize that additional ranges of fiber thickness in diameter measurements or in denier are contemplated and are within the present disclosure. In one specific embodiment, the device comprises 480 of 6 denier SCF fibers in a bundle and a crossing profile of 0.033 inches (2.5 French).

Further characterization of the fibers can barrow from the approaches outlined in the '248 patent. In particular, the overall capillary sizes can be characterized. In some embodiments of interest, the fibers have a specific capillary volume of at least about 0.5 cc/g, in other embodiments at least about 1.0 cc/g, in further embodiments at least about 2.0 cc/g and in additional embodiments at least about 3.0 cc/g. Also, the specific capillary surface area can be at least about 500 $cm^2/g$, in some embodiments at least about 1000 cm$^2$/g, in further embodiments at least about 2000 cm$^2$/g, and in other embodiments at least about 3000 cm$^2$/g. A person of ordinary skill in the art will recognize that additional ranges of capillary volumes and capillary surface areas are contemplated and are within the present disclosure. Test methods for evaluating the specific capillary volume, the specific surface capillary area and the adhesion tension are described in detail in the '248 patent, which is incorporated herein by reference for the explicit description of the determination of these values.

It has been discovered that particular preparation processes for the fibers can lead to significantly improved uniformity of the performance of the embolism protection device. In particular, the fibers are twisted within the fiber bundle. In some embodiments, heat is also applied to the fibers. While any degree of twist can be desirable, twist can be applied to the fiber bundle of at least about 5 degrees and in further embodiments from about 180 degrees to about 360 degrees. Furthermore, multiple rotations, for example, about 360 degrees to about 1080 degrees, can further act to increase the density of fibers and may be advantageous. A person of ordinary skill in the art will recognize that additional ranges of twist within the specific ranges above are contemplated and are within the present disclosure. The twist can be applied by fastening one end of the fiber bundle, applying the twist and fastening the other end of the fiber bundle. A suitable torque coupler can facilitate the application of the twist to the fibers since the corewire does not rotate due to tension in the SCF fibers. This is described more specifically below with respect to a specific embodiment. With the application of a suitable twist, the embolism protection device is observed to perform with essentially uniform performance. Without the application of the twist, some of the fiber devices are observed to have small gaps in the filtering of the flow upon deployment. Thus, the twist provides for a commercial device with reproducible performance expected for medical devices in practice.

Specific Embodiments with a Fiber-Based Embolism Protection Structure within an Integrated Guiding Device To summarize how various features can work together within an integrated guiding device, two specific embodiments of an integrated guiding device comprising an embolism protection structure is described in some detail. These devices are based upon the embolism protection structure similar to the structure in FIGS. 23-25 with specific features of the torque coupler specified. Referring to FIG. 26, integrated guiding device 450 comprises hypotube 452, corewire 454, torque coupler 456, embolism protection device 458, proximal coil 460, and distal coil 462. Torque coupled 456 comprises corresponding structural features in hypotube 452 and corewire 454 that interface to form the torque coupler. This embodiment is dimensioned to reach coronary arteries from a vein in the patient's thigh using conventional catheter procedures. In general, the device can be inserted through an incision in, for example, a patient's thigh, arm or neck. In general, the integrated guide device can be placed at various desired locations within a patient's arterial vasculature.

Referring to FIGS. 27A and 27B, hypotube 452 comprises notch 470 that forms a portion of the torque coupler 456. Apart from notch 470, hypotube 452 is a stainless steel tube with a constant inner diameter (0.0085±0.001 inches) and outer diameter of 0.014 inches. In this embodiment, hypotube 452 has a length of 60.5 inches. Stainless steel is convenient due to cost, biocompatibility and mechanical properties, but other materials and other dimensions can be used, as described above. Referring to FIG. 28, 1 inch at the distal end 472 of hypotube 452 is machined down to an outer diameter of 0.0125 inches with an approximately linear taper 474 over 0.25 inches between the 0.014 inch and the 0.0125 inch outer diameters. Proximal coil 460 is welded or otherwise bonded to the distal end 472 of hypotube 452, as shown in FIG. 28. Proximal coil 460 has an outer diameter of about 0.0125 inches and an inner diameter of about 0.009 inches.

Referring to FIG. 26, corewire 454 comprises a pull 480 fastened with a solder ball 482 at its proximal end. Corewire 454 also comprises a solder ball 484 at its distal end to maintain distal coil 462 on the corewire. The corewire is a stainless steel wire with a diameter of 0.0085 inches. Corewire 454 is coated with polytetrafluoroethylene to a maximum diameter of 0.0087 inches except for the distal about 2 inches, which is uncoated. Referring to FIGS. 27A, 27B, 29 and 30, corewire 454 has a flattened key portion 486 that forms a portion of torque coupler 456. Key portion 486 has a length of about 1 inch along the wire with a distal edge about 13.75 inches from the distal end of corewire 454. Referring to FIGS. 29 and 30, distal end 490 of corewire 454 is tapered over a distance of 1.485 inches. The distal 0.47 inches tapered distal end 490 is stamped to flatten the tip 492 in the same plane as the flattened key portion 486, as shown in the side views of FIGS. 29 and 30. Flattened tip has a width of 0.0075 inches and a thickness of about 0.0016 inches. Distal coil 462 fits over about the distal 1 inch of corewire 454. Corewire 454 has attachment elements 494, 496, 498 to facilitate attachment of distal coil 462 and filter structure 458.

Figure 31:
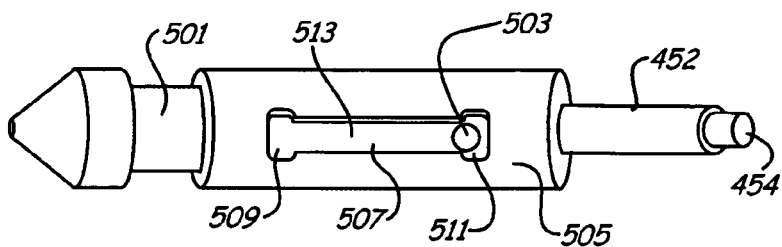
FIG. 31 is a fragmentary, side perspective view of the device of FIG. 26 with an alternative actuating tool.

An alternative embodiment of the pull element is shown in FIG. 31. Collet 501 is attached at the end of corewire 454, and push button 503 is placed near collet 501. A sliding collet 505 is fastened to hypotube 452. Sliding collet 505 has a slot 507 extending through its wall with enlarged openings 509, 511 at the ends of a linear section 513. Button 503 is depressed when aligned with linear section 513, but button 503 can extend outward at enlarged openings 509, 511 relative to its depressed configuration when aligned with linear section 513. Thus, the interface of sliding collet 505 with button 503 provides for two locked positions with a sliding motion between them. Sliding collet 505 and push button 503 function together as an actuation element for the embolism protection device through the control of the movement of corewire 454 with respect to hypotube 452. When button is in bulge 511, the embolism protection device is locked in a low profile delivery/recovery configuration. When button is in enlarged opening 509, the embolism protection device is locked in its deployed configuration. In general, for any of the embodiments of backend tools/pull elements, the tool can jacket the corewire such that the corewire within the tool cannot bend. In other words, the backend tool can surround the portion of the corewire interfacing with the tool. Thus, the backend tool can provide desired protection against unwanted kinking of the corewire that can result, in particular, when the corewire is moved relative tot he tube.

Notch 470 fits within flattened key portion 486 to form torque coupler 456. Torque coupler 456 is shown in detail in FIGS. 27A-27C. Once torque coupler 456 is fully formed, the longitudinal motion of corewire 454 is limited within hypotube 452 such that sufficient movement of corewire 454 relative to hypotube 452 to control embolism protection device 458 while limiting complications due to unwanted movement of corewire 454. However, the relative motion of corewire 454 with respect to hypotube 452 can also be limited by an actuating tool or other structure at the proximal end of the elements. The formation of torque coupler 456 is described further below. To form the key portion along the corewire, the corewire is placed within a block fixture 500, shown in FIGS. 32, 33 and 34. Block fixture 500 has a partial circular channel 502. When placed within channel 502, a portion of the corewire extends above the surface of the block. By grinding the wire to the surface of block fixture 500, the flattened key is formed in corewire 454. Block fixture 500 can be formed from stainless steel.

Embolism protection structure 458 connects between corewire 454, proximal coil 460 and distal coil 462. Referring to FIG. 35, a marker band 498 abuts the distal end of proximal coil 460, about 1.6 inches from the distal end of corewire 454. Marker band 498 can be formed from a radio-opaque material such that it can be viewed using x-rays for determining position within the patient's body. Suitable radio-opaque materials include, for example, radio-opaque polymers. Radio-opaque polymers include, for example, iodinated and brominated polymers, as described in U.S. Pat. No. 6,475,477 to Kohn et al., entitled "Radio-Opaque Polymer Biomaterials," incorporated herein by reference. Marker band 498 is attached near the proximal end of the filter cartridge structure 458. Embolism protection structure 458 comprises a fiber bundle 510 bound with bands 512, 514. At its proximal end, the fiber bundle is bound over a polymer tube 516 that rides over corewire 454. Adhesive 518 binds fiber bundle 510 to polymer tube 516, marker band 498 and proximal coil 460 at its proximal end, and to corewire 454 and distal coil 462 at its distal end.

To form the device, a filter cartridge comprising fiber bundle 510, bands 512, 514 and tube 516 is fed over corewire 454 and the corewire is fed through hypotube 452. The distance from the distal end of corewire 454 is measured to locate the flat grind of the corewire within hypotube 452. Hypotube 452 is placed within a fixture designed to control the amount of crimp. The parts are aligned longitudinally based on marking on corewire 454. Hypotube 452 is crimped to corewire 454 to form torque coupler 456. The tube and corewire are then longitudinally locked with limited longitudinal motion provided. The distal end of the filter cartridge is then fastened with adhesive to corewire 454. The fiber cartridge is twisted and the proximal end of the fiber cartridge is bonded with adhesive to proximal coil 460. The torque coupling of the corewire to the hypotube and proximal coil prevent rotation that would undo the twist in the fiber cartridge.

The second specific embodiment of the integrated guiding device is the same as the embodiment in FIGS. 26-35 except for the torque coupling feature of the corewire and for the actuation element. Specifically, the design of the sliding collet and the corewire result in the rotation of the corewire relative to the hypotube while the embolism protection device is deployed. This rotation of the fiber-based embolism protection device provides for even more consistent deployment of the fibers across the vessel.

Figure 36:
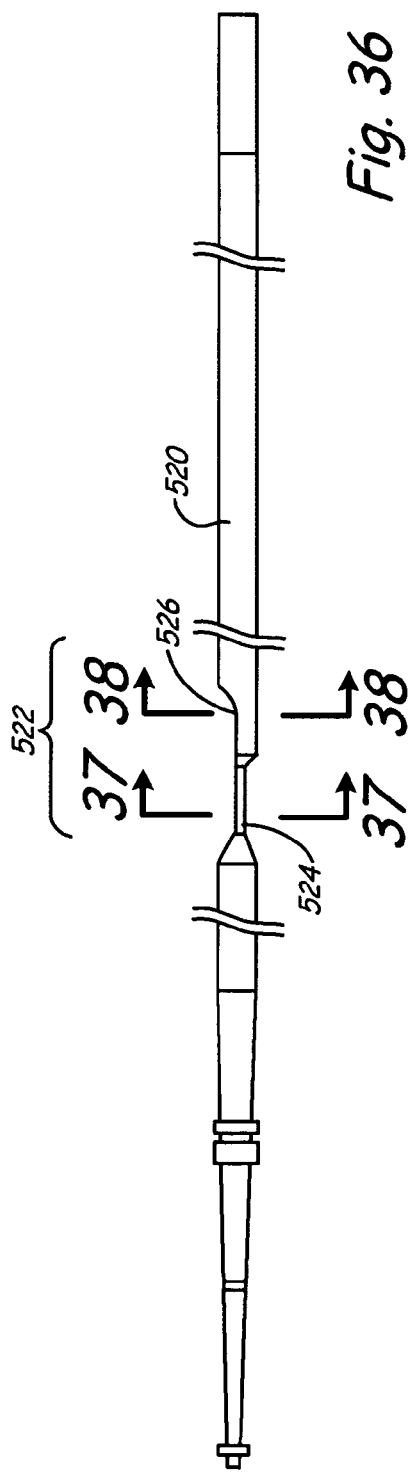
FIG. 36 is a side view of an alternative embodiment of the corewire.
Figure 38:
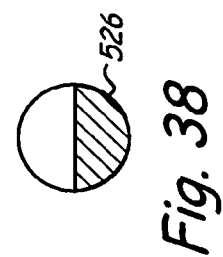
FIG. 38 is a sectional view of the corewire of FIG. 36 taken along line B-B of FIG. 36.
Figure 37:
FIG. 37 is a sectional view of the corewire of FIG. 36 taken along line A-A of FIG. 36.

Referring to FIG. 36, corewire 520 has the same structure as corewire 454 except that flattened key portion 486 is replaced with deployment guide 522. Deployment guide 522 comprises a thin section 524 and a key section 526. Sectional views of thin section 524 and key section 526 are shown in FIGS. 37 and 38, respectively. Thin section 524 has a diameter that is smaller than adjacent section of corewire 520 such that thin section 524 avoids contacting notch 470 of hypotube 452 when they are positioned at a common longitudinal position. Key section 526 has a similar cross sectional structure as flattened key portion 486. Key section 526 provides for torque coupling while thin portion 524 provides for rotation of the corewire 520 relative to hypotube 452 of FIG. 26. Thin section 524 and key section 526 can be formed, for example, analogously to flattened key portion 486, as described above.

Figure 39:
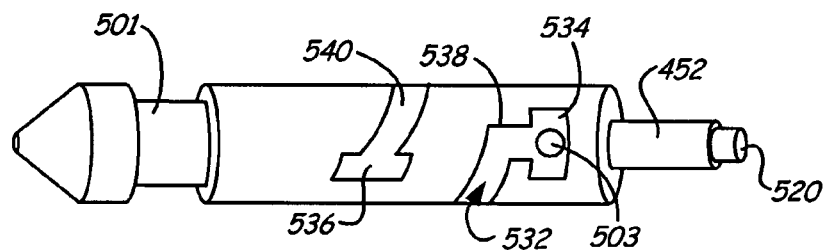
FIG. 39 is a fragmentary, side perspective view of a second alternative acutating tool for use with the corewire of FIG. 36.

Referring to FIG. 39, rotating collet 530 replaces sliding collet 505 for interfacing with the embodiment of corewire 520 in FIG. 36. Rotating collet 530 similarly is attached to hypotube 452. Rotating collet 530 has a rotating slide 532 extending through the walls of the collet. Rotating slide 532 has a first enlarged opening 534, a second enlarged opening 536, linear slide section 538 and a corkscrew slide section 540. Push button 503 is depressed when aligned with linear slide section 538 or corkscrew slide section 540. Push button 503 extends outward when aligned with enlarged opening 534 or enlarged opening 536 relative to its position when aligned with slide sections 538, 540. Thus, corewire 520 is locked relative to hypotube 452 when pushbutton 503 is aligned with enlarged openings 534, 536. Corewire 520 can move relative to hypotube 452 when push button 503 is aligned with slide sections 538, 540.

For the placement of the embolism protection device, push button 503 is positioned in enlarged opening 534 with the embolism protection device locked in a low profile configuration. Once the device is positioned as desired within the patient for deployment of the device, push button 503 is depressed, and transit of the push button along linear slide 538 provides for notch 470 to disengage from key section 526. As push button 503 moves along corkscrew slide section 540, corewire 520 is rotated relative to hypotube 452. Since notch 470 is then positioned at thin section 524, the rotation of hypotube 452 relative to corewire 520 can be transmitted to their distal end to rotate the fibers of an embolism protection device while it is being deployed. When pushbutton 503 reaches extended opening 536, the push button projects into extended opening 536, and the embolism protection device is locked in its deployed position. This process can be reversed to put the embolism protection device into a recovery configuration.

Figure 40:
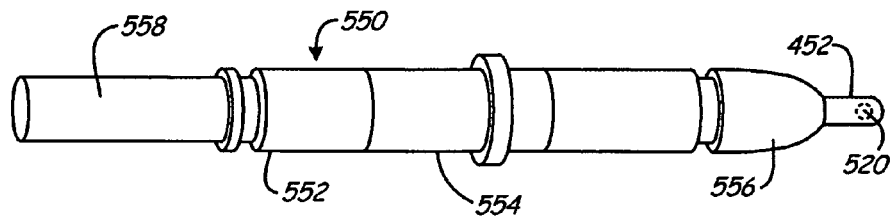
FIG. 40 is a side perspective view of an alternative embodiment of a pull element in an open configuration.
Figure 41:
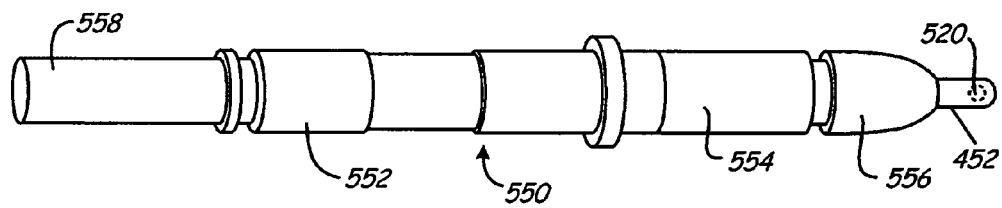
FIG. 41 is a side perspective view of the pull element in FIG. 40 in a closed configuration.

As noted above, in embodiments in which the corewire has friction with the tube, a backend tool can be used that has no locking features. Thus, another alternative embodiment to the pull element or backend tool of FIG. 31 is shown in FIGS. 40 and 41. Pull element 550 comprises a slide 552 and a body 554. Body 554 is fastened to a tube with collar 556 holding body in contact with the tube. Similarly, collet 558 grips the corewire and is fastened to slide 552. Thus, the relative movement of slide 552 with respect to body 554 moves the corewire relative to the tube. As shown in FIG. 40, pull element 550 is shown in an open position with the corewire sifted to its maximum extent in the distal direction relative to the tube, while in FIG. 41 pull element 550 is shown in its actuated or closed position with the corewire positioned to its full extent in a proximal direction relative to the tube. Since the pull element does not lock in any position, the corewire can be continuously positioned in any desired intermediate position.

Figure 42:
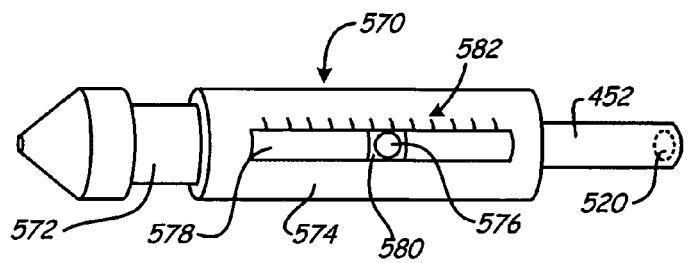
FIG. 42 is a side perspective view another alternative embodiment of a pull element with continuously adjustable locking.

Another alternative pull element is shown in FIG. 42. In this embodiment, pull element 570 has a slide 572 and a body 574. Body 574 is secured to tube 452, while slide 572 is secured to corewire 520. Thus, the relative movement of slide 572 with respect to body 574 controls the relative position of corewire 520 with respect to tube 452. Button 576 is attached to slide 572. Button 576 is constrained within slot 578 to provide for the limits of the movement of slide 572. Button 576 is spring loaded and controls the actuation of frictional flange 580. When button 576 is depressed, frictional flange 580 is deflected, and slide 572 can move relative to body 574. When button 576 is released, frictional flange 580 engages body 574 to resist any motion of slide 572 relative to body 580. Thus, pull element 570 can effectively provide continuous locking of the corewire at a selected position of corewire. Markings 582, such as tick marks, can be used to indicate desired positioning of button 576 for a deployment of an embolism protection device in particular sized vessels or to match other selected conditions for actuation of a particular medical device.

Figure 43:
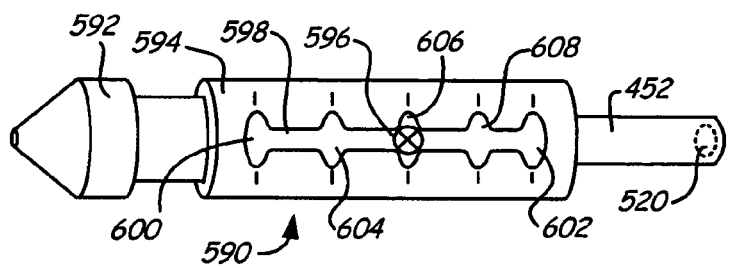
FIG. 43 is a side perspective view of a further alternative embodiment of a pull element with intermediate locking positions between the limits of the range of motion.

While continuously adjustable positioning can be advantageous, other types of intermediate positioning may also have desirable features in some embodiments. In general, some embodiments have one intermediate stop point as well as stop points at the two ends of the range of motion, while in other embodiments there are more than one intermediate stop points with the number of stop points selected as desired. Referring to FIG. 43, an embodiment is shown with a ratchet style pull element 590. Pull element 590 comprises slide 592 and body 594. Button 596 is attached to slide 592. Body 594 has a slot 598 that constrains the position of button 596. In this embodiment, slot 598 has two end stop points 600, 602 and three intermediate stop points 604, 606, 608. Marking 610 label the particular stop points. The operator can select the particular stop point to position corewire 520 at one of the end points of its range of motion or at an intermediate stop point. Friction based ratchet structures can be similarly used. In other embodiments, one intermediate stop points, two intermediate stop points, four intermediate stop points, five intermediate stop points, ten intermediate stop points, 20 intermediate stop points, or any number in between can be used as an alternative tot he three intermediate stop points shown in FIG. 43 based on the disclosure herein.

Surgical System

In addition to the systems designed for less invasive procedures, medical components for filtration can be effectively incorporated into a surgical system for use in procedures within vessels exposed during the surgical procedure. In particular, the surgical systems can have a filter at the end of a guide structure for placement within the vessel, such as a blood vessel. While various guide structure can be used, the surgical system can comprise an integrated guiding device as described herein, such as an integrated guiding structure with torque coupling between a corewire and a corresponding tube. The surgical system can further comprise an aspiration catheter that can be used to facilitate removal or recovery of the filter with reduced chance of downstream release of emboli during the recovery process. In some embodiments, the surgical system further comprises a cannula to facilitate placement of the filter within the vessel.

The surgical systems can have certain modifications relative to corresponding systems for less invasive procedures performed with catheter-based components. These modifications can quicken the procedure, which can be particularly significant for surgical procedures in which the patient may be under general anesthesia as well as possibly a shunt and/or cardio-pulmonary bypass, which can involve conditions in which the prognosis may be improved by shortening the procedure time. Also, for many surgical procedures, the guide structure can be shorter, such as no more than about 100 cm (39.4 inches), in other embodiments from about 30 cm (11.8 inches) to about 90 cm (35.4 inches) and in further embodiments from about 45 cm (17.7 inches) to about 60 cm (23.6 inches). The outer diameter of the guide structure may or may not be 0.014 inches, the standard diameter for certain guidewire applications for less invasive procedures. A person of ordinary skill in the art will recognize that additional ranges of lengths within the explicit ranges are contemplated and are within the present disclosure.

Due to the use of the system on an exposed vessel, most of the length of the guide structure is outside of the patient during the procedure. Since the length of other components associated with the system similarly do not need to be too long, these devices can be shifted along the length of the guide structure for use when needed and away from the vessel when not needed. These other devices include, for example, an aspiration catheter and/or a cannula. Thus structures do not need to be back loaded onto or off from the guide structure during the procedure, which can involve disconnecting and reconnecting a pull element or other backend tool associated with the guide structure.

Figure 44:
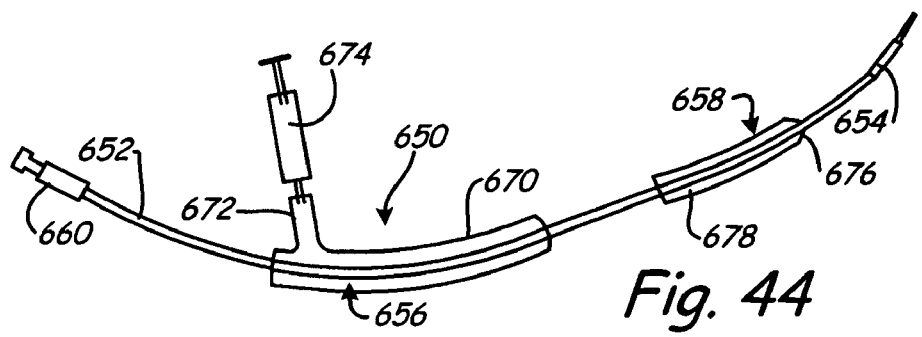
FIG. 44 is a schematic top view of a surgical system for placement of a filter within an exposed vessel.

An embodiment of a surgical system is shown in FIG. 44. Surgical system 650 comprises a guide structure 652, a filter element 654 attached at or near the distal end of guide structure 652, an aspiration catheter 656 and an optional cannula 658. Guide structure 652 can be a guide wire, although in some embodiments of particular interest, guide structure 652 comprises an integrated guiding device with torque coupling, such as the embodiments described above. Guide structure 652 can have a backend tool 660 to facilitate handling of guide structure 652, and backend tool 660 can be pull element, such as the pull elements described above, for embodiments involving an integrated guide structure in which the pull element facilitates the relative movement of the corewire relative to the tube of the integrated guide device. Filter element 654 can have any reasonable design that provides for filtered flow of bodily fluids flowing through the structure. In some embodiments of particular interest, filter element 654 can be a fiber-based filter element such as filter element 404 in FIGS. 22-25 or filter element 458 in FIGS. 26 and 35.

Aspiration catheter 656 generally comprises a generally tubular section 670, a suction port 672 and a suction device 674. Tubular section 670 has an internal lumen through which suction is applied through a distal opening. Suction port may or may not comprise a fitting that provides for reversible attachment of the suction device. Suitable fittings include, for example, a Leur lock fitting. Suitable suction devices include, for example, a syringe, a pump, a compressed bladder or the like. Structures of aspiration catheters generally useful for the recovery of embolism protection devices are described further in copending U.S. patent application Ser. No. 10/854,920 to Galdonik et al., entitled "Emboli Filter Export System," incorporated herein by reference. For surgical applications, the aspiration catheter generally can have an over the wire design, although the rapid exchange designs described in application Ser. No. 10/854,920 can be used if desired.

For use with a surgical system, the aspiration catheter can incorporate a design that is somewhat different than the design of a catheter for use with a less invasive system. For use with less invasive systems, the aspiration catheter extends a significant distance within the patient and has a corresponding suitable length which suggests mounting and dismounting of the aspiration catheter from the guide structure as needed. In contrast, for use with a surgical system, the aspiration catheter does not need to extend far into the patient's vessel. Thus, the aspiration catheter generally can have a length less than 75 cm (29.5 inches), in further embodiments from 5 cm (2.0 inches) to 50 cm (19.7 inches) and in other embodiments from about 8 cm (3.1 inches) to about 40 cm (15.7 inches). In some embodiments, the length of the aspiration catheter is no more than ¾ of the length of the guide structure, in further embodiment no more than 60 percent, and in other embodiment no more than about 30 percent of the length of the guide structure. If the length of the aspiration catheter is sufficiently short relative to the length of the guide structure, the aspiration catheter can be mounted onto the guide structure prior to initiation of the procedure and place out of the way until it is desired to place the distal end of the aspiration catheter within the patient's vessel. Avoiding the mounting and/or removal of the aspiration catheter over the guide structure during the procedure can advantageously reduce the time of the procedure. In some embodiments, the average outer diameter of tubular section 670 ranges from about 0.010 inches to about 0.090 inches and in additional embodiment from about 0.030 inches to about 0.055 inches. A person of ordinary skill in the art will recognize that additional ranges of dimensions of the aspiration catheter within the explicit ranges above are contemplated and are within the present disclosure.

The aspiration catheter can have an expanded compartment at its distal end to facilitate the withdrawal of an embolism protection device into the aspiration catheter during retrieval. The optional expanded compartment can be formed from an elastic material, such as a spring metal or polymer. In some embodiments, the distal expanding chamber has one or more slits cut within the material to facilitate expanding of the chamber. In some embodiments, the expanded distal chamber has an outer diameter at least about 20 percent greater than the average diameter of the shaft of the aspiration catheter within about 10 centimeters of the expanded compartment. The distal opening generally has a corresponding size as the expanded compartment. Aspiration catheters with an expanded compartment for embolism protection device retrieval are described further in copending U.S. patent application Ser. No. 10/854,920 to Galdonik et al., entitled "Emboli Filter Export System," incorporated herein by reference.

Cannula 658 comprises a pointed tip 676 and a channeled portion 678 through which guide structure 652 can pass. In some embodiments, filter element 654 is inserted through an incision in a vessel and a cannula may not be used. In other embodiments, cannula 658 is inserted through the wall of the vessel using pointed tip 676 for the placement of filter 654 into the vessel. While in general any reasonable cannula structure can be used, certain cannula designs facilitate the performance of the surgical procedure. In particular, it is desirable not to have to remove and/or place the aspiration catheter onto and/or off from the guide structure during the procedure. Therefore, the length of the cannula should be small such that the sum of the length of the cannula and the length of the aspiration catheter are less than the length of the guide sturcture. Furthermore, for embodiment of particular interest, the cannula has a small enough outer diameter such that the aspiration catheter can pass over the cannula, or the cannula has a variable outer diameter for example with a slit such that the cannula diameter can be physicall reduced to pass the aspiration catheter past the cannula, or the cannula has a slit such that the cannula can be straightforwardly and quickly placed over the guide structure and removed from the guide structure after use. Since the cannula generally is not used to draw liquid or restrict the flow of liquid, the cannula can have a slit along its length without interfering with its function.

In general, the surgical system can be used in combination with procedures on any exposed bodily vessel, such as urinary track vessel or blood vessels. The procedure is initiated by exposing the vessel. The filter can then be positioned early enough in the procedure to trap emboli within the vessel at stages of the procedure in which emboli may be generated. The filter is removed from the vessel at an appropriate point in the procedure. Aspiration can be applied during the filter recovery to reduce the risk of emboli escaping down stream during recovery of the filter. The filter can be drawn partly or completely within the aspiration catheter during the recovery process.

In some specific embodiments, after the vessel is exposed, a purse-string suture is tied around the proposed access site. A purse-string suture is a continuous suture line that can be tightened at a selected time to cinch the hole closed. Then, a cannula is inserted into the sidewall of the vessel, either with or without suction. A wire can be advanced into the vessel to confirm that the cannula is completely into the vessel. Once this is verified, the wire is removed. This procedure with the cannula is referred to commonly as the Seldinger Technique.

Once the vessel is available, the filter is inserted into the cannula and advanced downstream. Then, the cannula is retracted and parked on the guide structure or removed from the guide structure. The filter can be deployed once in position. At this point, surgery is generally performed upstream from the filter. After the risk of emboli generation is sufficiently complete, the aspiration catheter is advanced into a position with the tip of the catheter near the filter. While aspiration is being applied, the filter is retracted and pulled into the distal opening of the aspiration catheter. The aspiration catheter and the filter are then removed from the vessel. Aspiration generally is stopped some time after the filter is within the aspiration catheter. After the aspiration catheter is removed, the purse-string suture is closed and tied.

Figure 45:
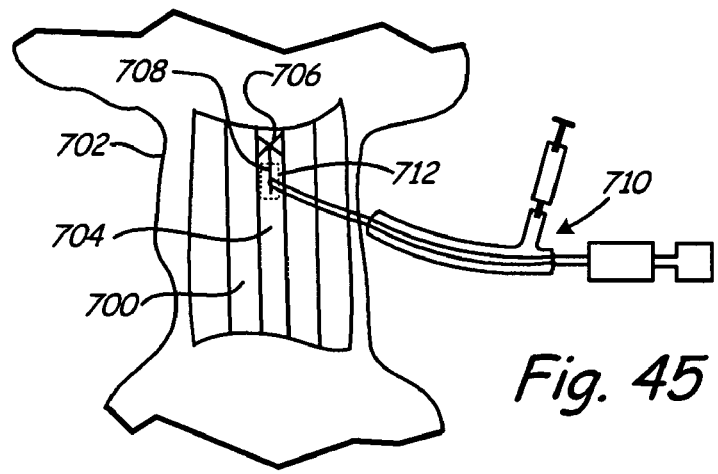
FIG. 45 is a schematic view of a surgical system used during a carotid endarterectomy.

The surgical systems described herein are of particular interest for the performance of certain high risk procedures. For example, the surgical systems can be used effectively for the performance of carotid endarterectomy. This procedure is performed in the neck of a patient to clear carotid arteries, for example with the delivery of a stent. Clearly, it is undesirable for emboli to be released downstream into the brain since these can result in strokes of varying severity. Referring to FIG. 45, an incision 700 in a patient's neck 702 exposes carotid artery 704. A filter 706 attached to guide structure 708 is deployed within carotid artery 704. Filter 706 and guide structure 708 are components of surgical system 710. Guide structure 708 inserts through an opening surrounded with a purse-string suture 712.

Figure 46:
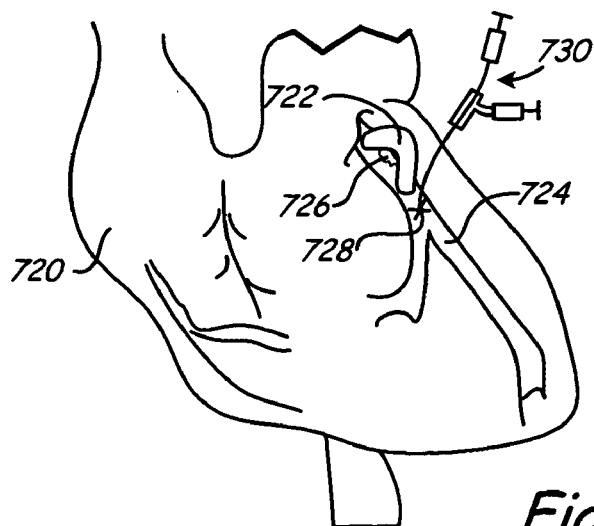
FIG. 46 is a schematic view of a surgical system being used during a coronary artery bypass grafting procedure.

In addition, the surgical systems can be used effectively during procedures to anastamose or interconnect a graft to an artery. For example, coronary artery bypass grafting is used to circumvent blockages in the coronary arteries. A filter can be used to trap any emboli released during the procedure. In some embodiments, the device is passed through an anastomosis. Referring to FIG. 46, a patient's heart 720 is shown with a vessel graft 722 connected to a coronary artery 724 to bypass a blockage 726. A filter 728 is placed upstream from the graft attachment points. Filter 728 is a component of surgical system 730.

Distribution and Packaging

The medical devices described herein are generally packaged in sterile containers for distribution to medical professionals for use. The articles can be sterilized using various approaches, such as electron beam irradiation, gamma irradiation, ultraviolet irradiation, chemical sterilization, and/or the use of sterile manufacturing and packaging procedures. The articles can be labeled, for example with an appropriate date through which the article is expected to remain in fully functional condition. The components can be packaged individually or together.

Various devices described herein can be packaged together in a kit for convenience. The kit can further include, for example, labeling with instruction for use and/or warnings, such as information specified for inclusion by the Food and Drug administration. Such labeling can be on the outside of the package and/or on separate paper within the package.

The embodiments above are intended to be illustrative and not limiting. Additional embodiments are within the inventive concepts. Although the present invention has been described with reference to particular embodiments, workers skilled in the art will recognize that changes may be made in form and detail without departing from the spirit and scope of the invention.

We claim:

1. A method for using a filter element attached to a guide structure within a vessel of a patient, the method comprising:
    inserting the filter element into the vessel wherein the guide structure comprises a corewire and a tube with an inner lumen over at least substantial length of the corewire, the filter element comprises a plurality of polymer fibers in a bundle comprising a first end constrained to the corewire and a second end constrained to the tube;
    deploying the filter element by moving the corewire relative to the tube to transition the filter element from a low profile configuration to an extended configuration that extends outward from the axis of the guide structure relative to the low profile configuration to form a three dimensional filtration matrix following insertion of the filter element;
    delivering a distinct treatment device into the vessel over the guide structure;
    performing a treatment procedure within the vessel using the distinct treatment device after the filter element is deployed to the three dimensional filtration matrix and prior to the application of suction;
    transitioning the filter element from the extended configuration to a removal configuration by changing the relative positions of the corewire and the tube; and
    applying suction during at least a portion of the process of transitioning of the filter element to the removal configuration through an aspiration catheter that is loaded over the guide structure.

2. The method of claim 1 wherein the removal of the filter element comprises withdrawing the filter element at least part way into an aspiration catheter.

3. The method of claim 2 wherein suction is applied during the transition of the filter element from the extended configuration to a removal configuration and during withdrawal of the filter element at least part way into the aspiration catheter.

4. The method of claim 1 wherein the filter element is inserted to capture emboli generated during an anastomosis procedure.

5. The method of claim 1 wherein the filter element is inserted to capture emboli generated during a carotid endarterectomy.

6. The method of claim 1 wherein the treatment procedure comprises the delivery of a stent.

7. The method of claim 1 wherein the treatment procedure comprises the deployment of a balloon.

8. The method of claim 1 wherein the distinct treatment device is delivered over the guide structure.

9. The method of claim 1 wherein the guide structure comprises a coil connected around a core wire distal end distal to the filter element.

10. The method of claim 1 wherein the corewire is solid.

11. The method of claim 1 wherein the aspiration catheter is loaded over the guide structure in a rapid exchange configuration.

12. The method of claim 1 wherein the fibers are surface capillary fibers.

13. The method of claim 1 wherein the fibers are twisted within the fiber bundle for at least 5 degrees.

14. The method of claim 1 wherein the distal half of the tube comprises a plurality of slots oriented transverse to the axis of the tube.

15. The method of claim 14 wherein the slots penetrate through the tube to the inner lumen.

16. The method of claim 1 wherein the tube comprises a key way within the lumen having a surface with an asymmetrical cross section and the corewire comprises a key having a surface with an asymmetrical cross section complimentary to the asymmetrical cross section of the key way surface.

17. The method of claim 1 wherein the guide structure further comprises a backend tool that controls the relative position of the corewire relative to the tube over a range of motion.

18. The method of claim 17 wherein the corewire within the tube has at least one stable position effectively locking the relative position between the end points of the range of motion.

19. The method of claim 1 wherein the corewire has a bend that provides friction against the tube wherein the friction provides the effective locking of the corewire.

20. The method of claim 1 wherein the guide structure has a length of no more than about 100 centimeters.

21. The method of claim 1 wherein the suction is applied with a syringe that is attached at a port of the aspiration catheter.

22. The method of claim 1 wherein a cannula having a central lumen and a pointed tip is mounted over the guide structure to facilitate insertion of the filter element and guide structure into the patient's vessel.

23. The method of claim 22 wherein the cannula has a slit to provide for placement and removal from a position with the guide structure within the central lumen of the cannula.

24. The method of claim 22 wherein the cannula has a range of adjustable outer diameters less than the inner diameter of the aspiration catheter.

* * * * *

UNITED STATES PATENT AND TRADEMARK OFFICE
CERTIFICATE OF CORRECTION

| | | |
|---|---|---|
| PATENT NO. | : 8,092,483 B2 | Page 1 of 1 |
| APPLICATION NO. | : 11/072001 | |
| DATED | : January 10, 2012 | |
| INVENTOR(S) | : Jason Galdonik et al. | |

It is certified that error appears in the above-identified patent and that said Letters Patent is hereby corrected as shown below:

IN THE CLAIMS:

Column 30, Line 24, Claim 17, should read:
Claim 17. The method of claim 1 wherein the guide structure further comprises a backend tool that controls the ~~relative~~ position of the corewire relative to the tube over a range of motion.

Column 30, Line 28, Claim 18, should read:
Claim 18. The method of claim 17 wherein the corewire within the tube has at least one stable position effectively locking the relative position between [[the]] first and second end points of the range of motion.

Column 30, Line 32, Claim 19, should read:
Claim 19. The method of claim 1 wherein the corewire has a bend that provides friction against the tube wherein the friction provides [[the]] effective locking of the corewire position within the tube.

Signed and Sealed this
Fifth Day of June, 2012

David J. Kappos
*Director of the United States Patent and Trademark Office*